(12) United States Patent
Kovanen

(10) Patent No.: US 12,377,281 B1
(45) Date of Patent: *Aug. 5, 2025

(54) MAGNETIC PULSE THERAPY DEVICE (MPTD) FOR THE TREATMENT OF PAIN

(71) Applicant: Innovator Corporation, Browns Point, WA (US)

(72) Inventor: David J Kovanen, Browns Point, WA (US)

(73) Assignee: Innovator Corporation, Browns Point, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/905,994

(22) Filed: Oct. 3, 2024

Related U.S. Application Data

(63) Continuation of application No. 18/432,044, filed on Feb. 4, 2024, now Pat. No. 12,268,891.

(51) Int. Cl.
*A61N 2/00* (2006.01)
*A61N 2/02* (2006.01)

(52) U.S. Cl.
CPC ............... *A61N 2/008* (2013.01); *A61N 2/02* (2013.01)

(58) Field of Classification Search
CPC .................................. A61N 2/008; A61N 2/02
See application file for complete search history.

(56) References Cited

U.S. PATENT DOCUMENTS

| 4,757,804 A * | 7/1988 | Griffith | A61N 2/02 607/51 |
| 2002/0151760 A1 * | 10/2002 | Paturu | A61N 2/02 600/15 |

* cited by examiner

*Primary Examiner* — Carrie R Dorna
*Assistant Examiner* — Joshua Daryl D Lannu
(74) *Attorney, Agent, or Firm* — Stevens Patent Law LLC; James Stevens

(57) ABSTRACT

For foot pain sufferers, especially those with peripheral neuropathy, this invention introduces a breakthrough device. Its key feature is a novel self-aligning applicator that simultaneously treats the entire foot and eliminates adjustments and sizing. A large enough and powerful enough treatment zone is possible by utilizing a segmented solenoid and by placing the foot directly into its coherent core flux. Dosages to the entire foot of $2{,}500\ \Sigma\Delta B_T$ can be achieved within an hour. Extremely low voltages are used, and very little heat is produced, making the device suitable for in-home use.

30 Claims, 13 Drawing Sheets

| mm | L123456 | L1 | L2 | L3 | L4 | L5 | L6 |
|---|---|---|---|---|---|---|---|
| | 90 | 91 | 92 | 93 | 94 | 95 | 96 |
| 0 | 32.0 | 31.2 | 12.6 | 5.6 | 3.4 | 2.2 | 1.4 |
| 10 | 38.0 | 37.0 | 17.4 | 7.6 | 4.0 | 2.4 | 1.8 |
| 20 | 42.4 | 36.4 | 23.0 | 9.8 | 4.8 | 2.8 | 1.8 |
| 30 | 43.6 | 29.2 | 29.0 | 13.0 | 6.0 | 3.4 | 2.2 |
| 40 | 43.2 | 21.6 | 33.0 | 16.8 | 7.6 | 4.0 | 2.4 |
| 50 | 44.0 | 15.4 | 31.0 | 22.4 | 10.0 | 5.0 | 3.0 |
| 60 | 43.0 | 11.4 | 25.0 | 27.8 | 13.2 | 6.6 | 3.6 |
| 70 | 42.2 | 8.2 | 18.6 | 30.2 | 17.2 | 8.4 | 4.4 |
| 80 | 40.4 | 6.2 | 13.6 | 27.2 | 22.4 | 10.8 | 5.4 |
| 90 | 42.2 | 4.6 | 10.0 | 21.6 | 26.8 | 13.8 | 6.6 |
| 100 | 39.4 | 3.6 | 7.6 | 16.6 | 27.6 | 17.8 | 8.6 |
| 110 | 38.6 | 3.0 | 5.8 | 12.6 | 24.0 | 22.8 | 11.0 |
| 120 | 37.4 | 2.5 | 4.6 | 9.4 | 18.8 | 26.6 | 14.0 |
| 130 | 36.0 | 2.0 | 3.6 | 7.2 | 14.6 | 25.6 | 17.8 |
| 140 | 34.4 | 1.8 | 3.0 | 5.6 | 11.4 | 23.4 | 22.6 |
| 150 | 30.2 | 1.4 | 2.4 | 4.4 | 8.8 | 16.8 | 25.6 |
| 160 | 26.8 | 1.4 | 2.0 | 3.4 | 6.6 | 13.0 | 23.8 |
| 170 | 21.2 | 1.2 | 1.8 | 3.0 | 5.2 | 10.0 | 19.6 |

MAGNETIC PULSE THERAPY DEVICE (MPTD) FOR THE TREATMENT OF PAIN

CROSS-REFERENCE TO RELATED APPLICATIONS

This continuation application claims the benefit of, and priority to, U.S. patent application Ser. No. 18/432,044, titled MPTD for the Treatment of Pain, and filed on Feb. 4, 2024, the entire application of which is incorporated herein by reference in its entirety.

ORIGIN OF THE INVENTION

The motivation for this invention stems from the inventor's personal experience with debilitating foot pain caused by idiopathic peripheral neuropathy.

In desperation when prescription medications failed to provide relief, several years ago he traveled to Asia where he underwent therapy using a high-power Magnetic Pulse Therapy Device (herein called an "MPTD") even though it was not then FDA approved for use in the United States. These treatments proved highly successful, leading to complete pain relief, although ongoing maintenance sessions continue to be required.

The MPTD in Asia was a large unit operating on voltages not deemed safe by the FDA for home use devices. Thus, the inventor has reduced to practice an MPTD with clinical effectiveness such that it can be safely and conveniently be used in the home.

This invention represents the culmination of extensive research involving thousands of hours and hundreds of prototypes in that pursuit. With a background spanning fifty years in electrical engineering and computer science, the inventor embarked on a mission to develop a better MPTD that could provide relief to millions of others who suffer similarly. This invention introduces a breakthrough device that has clinical-level efficacy, simplicity, safety, economy, and suitability for in-home self-administration.

BACKGROUND OF THE INVENTION

More than a million Americans suffer from severe neuropathic pain in their feet. More than a third of people with diabetes suffer chronic pain from Diabetic Peripheral Neuropathy (DPN). An estimated 20 million Americans suffer from plantar fasciitis.

Despite the well documented analgesic potential of MPTDs, their adoption for pain relief remains limited. As elaborated in the Prior Art section of this application, this limited adoption primarily stems from inherent technical issues and limitations associated with existing MPTDs. No commercially available MPTD currently possesses both FDA clearance for treating foot pain and meets the requisite safety requirements for self-administration and in-home use. This has unfortunately led to a proliferation of unauthorized devices (that range from sham devices to ones with severe design flaws) that are often promoted through clandestine channels. This proliferation underscores the persistent and unmet need for a safe, effective MPTD for pain management, with a focus on self-administration and in-home use.

TECHNICAL FIELD

This invention is a medical device to treat pain and other symptoms. While any type of pain may be treated, it is especially well suited for pain stemming from diabetic neuropathy (DN or DPN), peripheral neuropathy (PN), or chemotherapy-induced peripheral neuropathy (CIPN).

The invention uses dynamic magnetic fields (magnetic pulses) produced by electrically pulsed coils for treating humans or animals, where the magnetic field itself provides therapeutic benefit. MPTDs of this type are commonly but variously called Magnetotherapy (C61N), Repetitive Magnetic Pulse Stimulation (RPMS), Magnetic Peripheral Nerve Stimulation (mPNS), Transcranial Magnetic Stimulation (TMS), Pulsed Electromagnetic Field (PEMF), Pulsed Electromagnetic Transduction (PEMT), Electromagnetic Field Therapy (EMF), Magnetic Pulse Stimulation (MPS), Trans Cutaneous Magnetic Stimulation (TCMS), or by other names.

BACKGROUND ART

Magnetic Pulse Therapy Devices (herein "MPTD") used in the treatment of pain have a history that extends back about four decades. One of the earliest published studies was in 1982 by Polson. (POLSON, M.J.R., BARKER, A.T. & FREESTON, I.L. Stimulation of nerve trunks with time-varying magnetic fields. Med. Biol. Eng. Comput. 20, 243-244 (1982)). Hundreds or thousands of studies document that pain is safely reduced or eliminated through repetitive electromagnetic pulses. Outside the United States, MPTDs have been used clinically for pain relief for at least twenty years.

The FDA has cleared the use of MPTDs for the treatment of chronic neuropathic pain as well as other indications.

Strong repetitive magnetic pulses can induce an analgesic or antinociceptive effect with significant and sustained duration, even when pharmaceuticals have been ineffective. Studies have shown this pain relief to be effective in the majority of cases, with reductions in pain intensity ranging from 50% to 100%. The effects often last for weeks or months, and in some cases, some of the pain reduction may be permanent. There are no known adverse side effects from repetitive magnetic pulse stipulation.

Encouragingly, some persons with Diabetic Peripheral Neuropathy, a condition often characterized by both pain and numbness, report a partial regaining of feeling in areas previously devoid of sensation following MPTD therapy.

The exact biological mechanisms of MPTD pain relief are not well understood.

DESCRIPTION OF THE RELATED ART

Magnetic Pulse Parameters for Efficacy

Most studies have shown medical efficacy in treating pain with magnetic pulses having at least ten milli-Tesla of flux density ($B>10$ mT) but more consistently demonstrable results come from flux densities of at least 25 mT ($B \geq 25$ mT).

Magnetic pulses with a strength under 1 mT are inconclusive as to whether there is any medical benefit whatsoever (other than the placebo effect). It is not known why magnetic pulses weaker than 1 mT ($B<1$ mT) have generally not shown to have any conclusive medical benefit.

Medical efficacy appears to derive from the dosage, which is the total change in magnetic flux ($\Sigma \Delta B$) delivered. Higher power systems have shown the benefit of faster efficacy but not better overall efficacy. This is possibly because higher power systems quickly deliver necessary dosages and lower power systems can take 100 hours or more to deliver the same dosage as a single 20-minute high-power session.

In a clinical environment a typical treatment protocol will range between 15,000 $\Sigma\Delta B_T$ and 75,000 $\Sigma\Delta B_T$. That is, between 1,000 and 50,000 pulses with a flux density of 1.5T (1,500 mT) will be administered in a typical therapy session. (Math: 1,000 pulses×1.5T=1,500 $\Sigma\Delta B_T$ and 50,000 pulses× 1.5T=75,000 $\Sigma\Delta B_T$). Typically, 5 to 10 of these treatment sessions are required in the first month. At these power levels pain relief commonly happens within 5 to 10 sessions and can sometimes be apparent in a single session.

Studies have generally shown that pulse rise time is very important. Steep rise times of the magnetic flux ($\Delta B/dt$ or $dB/dt$) demonstrably perform better than sine waves. Square waves are often thought to be ideal, but other shapes such as a triangle, have shown efficacy. The prevailing understanding is that $\Delta B/dt$ is the second most important parameter after $\Delta B$, and thus, square waves with their steep rising and falling edges appear to be optimal.

It is widely accepted that pulses with durations (tp) of approximately 250 µS are optimal for the treatment of pain, although MPTDs variously produce pulses ranging from 10 to 500 µS. Very long pulse durations (tp>100 mS) have not shown benefit and may even be harmful. Very short pulses (tp<10 µS) do not seem to be as effective.

Magnetic pulses create an electrical charge within the cells being treated. Leaving a charge on cells is thought to be bad. The best-known way to leave a net zero cell charge is to use symmetric bipolar pulses that return to zero. An ideal pulse might be 125 µS followed immediately by an opposite polarity pulse of 125 µS. Bipolar pulses are required by some regulatory agencies.

Pulse frequencies vary considerably with magnetic pulse therapy. Frequencies over 100 Hz are discouraged both by regulation and the recommendations of the International Commission on Non-Ionizing Radiation Protection because high frequencies (KHz and MHz) can cause heating within the appendage being treated and have shown the possibility of DNA damage under some scenarios. For providing relief from neuropathic pain, frequencies between 1 and 100 Hz are most common.

Some companies marketing non-FDA cleared MPTDs claim that specific frequencies are "tuned" to certain ailments. Examples are 10 to 15 Hz for treating acne, 2 to 8 Hz for treating Alzheimer's, 5 Hz for constipation, and 6 Hz for erectile dysfunction. Or, sometimes Schumann resonances are promoted for their snake-oil like medicinal properties. U.S. Pat. No. 6,701,185 ('185) is rather ebulliently speculative in this way. There is simply no scientific evidence supporting these kinds of claims, no such indications are FDA cleared for treatment using an MPTD.

Most clinical systems now in use are high-power MPTDs that have a flux density of about 1,500±500 mT, produce bipolar pulses of 125 µS+125 µS, and at frequencies between 1 PPS and 200 PPS.

Formation of Magnetic Pulses & Challenges

Magnetic pulses are created by energizing a coil with electricity. The magnetic output of the coil is somewhat simply stated as the product of the number of turns in the coil winding (N) and the amperage (A). Thus, coil turns, and amperage are directly related.

The complication is that a coil has inductance (L) which impedes any change in amperage flowing through the coil. Thus, adding more turns creates more inductance which makes it increasingly difficult to send pulses of amperage through the coil. A typical coil in an MPTD may have 12 to 24 turns. This many turns have enough inductance to strongly resist allowing enough amperage to pass through. To force sufficient amperage through the coil requires a very high voltage (acting as pressure), that is commonly 500 to 1,000 volts.

The goal of having a fast magnetic flux rise time ($\Delta B/dt$) gives preference to coils with fewer turns which have less inductance. This biases MPTDs towards designs with more amperage.

Generating magnetic pulses in clinical strength high-power MPTDs commonly requires 500 to 1,000 volts and 1,000 to 10,000 amps, and typically the coil will be constructed of very thick wire, such as #2 through #8 AWG. Such power levels are instantly lethal and compliance with mandatory medical safety regulations such as IEC 60601 is quite challenging. This is also why high-power MPTDs are only suitable in a professionally supervised, controlled, clinical environment. It is also why these systems are expensive, large, and heavy.

BRIEF STATEMENT OF THE PRIOR ART

1) There remains an unmet and long felt need for an MPTD that can safely and effectively treat foot pain.

2) High-power MPTDs have medical efficacy. They are clinically proven to provide effective pain relief. However, they must be skillfully operated by a trained technician in a clinical setting because they employ lethal voltages and currents, are expensive, complicated, and are prone to thermal runaway.

3) Mid-power and low-power MPTDs have not been clinically shown to be effective at treating foot pain. It does not appear that they can plausibly deliver sufficient dosage levels in any reasonable way because of the low flux density and small applicator size.

4) There are many styles of applicators. None of them are optimal for a foot or similar appendage. Special-purpose applicators designed for the foot are implausible to construct, thermally dangerous, awkward to use, and in every case are suitable only for use in a clinical setting. Manually operated applicators do not deliver a uniform dosage, even when skillfully operated.

5) Existing applicators do not make good use of Core Flux, which is highly uniform, coherent, and potent.

6) No MPTD employs an applicator in the form of a solenoid formed by a multiplicity of axially aligned coils, with the treatment area within the solenoid.

7) There are no MPTDs suitable for in-home self-application and that have medical efficacy for treating foot pain by delivering required dosages to an entire foot.

SUMMARY OF THE INVENTION

The present invention discloses a Magnetic Pulse Therapy Device (MPTD) 20 that consistently delivers a medically effective dose of magnetic pulses ($\Sigma\Delta B$) for pain relief, that is inherently safe, that is simple to use and suitable for in-home self-application.

This is accomplished using a novel applicator 10 into which a foot 11 can be easily slid into and out of. This applicator consistently and precisely positions the foot within the core of a solenoid 15. The solenoid 15 is operatively formed by a multiplicity of axially aligned low-voltage coils 13 which collectively create a substantial volume of Core Flux 90, sufficient in size and strength to treat the entirety of the foot, concurrently. This design is inherently safe and reliable, employs no high voltages, has no possibility of thermal runaway, requires no skillful manipulation of an applicator, and is convenient enough to use frequently so that dosages with medical efficacy can be delivered.

To ensure clarity and brevity, the terms "appendage", "forefoot", "foot", "feet", "hand", "hands", "arm", and "leg" are used interchangeably throughout this description. The choice of one term over another is not intended in any way to limit the scope of the disclosed Magnetic Pulse Therapy Device (MPTD). Rather, the MPTD's design enables its application to any appendage suitable for receiving magnetic pulse therapy, regardless of the specific nomenclature employed.

DESCRIPTION

Achieving Medical Efficacy

Medical efficacy depends primarily upon delivering a medically effective dosage of magnetic flux ($\Sigma\Delta B$). The inability of mid-power and low-power MPTDs to deliver a sufficient dosage is a primary reason for their ineffectiveness. To establish that the present invention is capable of delivering a comparable dosage to that of a high-power machine requires quantification of dosing.

Leading hospitals in Asia using high-power MPTDs to treat neuropathic pain have various monthly maintenance treatment protocols ranging from 10,000 to 50,000 magnetic pulses with an average applied flux strength of 1.5T (1,500 mT). Therefore, monthly dosages range between 15,000 $\Sigma\Delta B_T$ and 75,000 $\Sigma\Delta B_T$. (Math: $10,000\Delta \times 1.5B_T = 15,000$ $\Sigma\Delta B_T$ and $50,000\Delta \times 1.5B_T = 75,000$ $\Sigma\Delta B_T$).

Note 1: $\Sigma\Delta B_T$ may be simply expressed as $\Sigma\Delta B$ as units of Tesla is the implied default unit.

Note 2: There is some temptation to incorrectly apply a percentage to dosage amounts, arguing that each pulse of a high-power system only treats a percentage of the foot. This temptation is incorrect. The correct approach is to determine the entire cumulative dosage applied to the entire foot. It is immaterial whether the $\Sigma\Delta B_T$ dosage is applied in small increments or concurrently.

A daily dosage of 500 $\Sigma\Delta B_T$ to 2,500 $\Sigma\Delta B_T$ is obtained by dividing the monthly amounts by 30 days. The entire foot would need to be treated with this dosage in order for the MPTD to have medical efficacy.

The Operative Solenoid

A solenoid 15 most typically consists of a single winding around a core for a meaningful and purposeful length. Coils 13 usually have a number of wraps of wire wound as tightly as possible to form a circle with as little length as possible. In the present invention an "operative solenoid" 15 (sometimes called simply a "solenoid" herein for brevity) means a series of axially aligned coils 13 which if energized concurrently would form Core Flux along a length of the coils 15, as does a typical solenoid and thereby collectively operate as a solenoid. (A solenoid such as this is also sometimes technically called a "segmented solenoid", although that term won't be used herein except in the Abstract where it is used to most succinctly describe the invention.) To accomplish this, the coils 13 may be either tightly wound or may actually be short solenoids themselves, with a meaningful and purposeful length. (Even though these coils 13 are technically short solenoids, they will be referred to as "coils" herein.)

A laboratory prototype established that a single 25 mm long coil 13 could produce a magnetic pulse with an average strength of 30 mT when energized with an Extremely Low Voltage (ELV) of 24 volts DC and using readily available automotive/industrial electronics.

Reaching a daily dosage of 2,500 $\Sigma\Delta B_T$ would therefore require at least 75,000 pulses. At a high pulse rate of 25 PPS (Pulses Per Second) it would take nearly one hour to treat just the area within this 25 mm coil. (Math: 2,500T $\Sigma\Delta B_T$ +30 mT: 25 PPS=55.5 minutes). This also numerically demonstrates why mid-power and low-power MPTDs have been largely ineffective at pain treatment: they are slow and don't cover much area.

The breakthrough was the realization that a sufficiently large operative solenoid 15 could be formed from a multiplicity of independent coils 13 that were axially aligned. It is the nature of Core Flux to form together with other Core Flux because of its high coherence and long coherence length. That is, stacking coils 13 allows them to have an additive effect: they reinforce each other's strength and collectively operate like a traditional solenoid. The average flux density within the length of the solenoid 15 was measured to be about 50% higher than the average of each separate coil 13. The flux density throughout these coils 13 is remarkably uniform 91-96 throughout the solenoid's length 15 because the flux has formed into true Core Flux. Importantly, strength of a solenoid 15 formed this way can be increased merely by adding coils 13; the strength increases in direct proportion to the number of coils 13.

After building hundreds of prototypes, it was established that it was feasible to construct an operative solenoid 15 from a reasonable quantity of independent axially aligned coils 13, each separately powered by 24 volts. Laboratory tests confirmed that the flux from the individual coils 13 did, in fact, form into powerful and coherent Core Flux throughout the length of the operative solenoid 15.

A test fixture consisting of six axially aligned coils 13 formed into a size and shape suitable to treat an entire forefoot, including the hallux 67, dorsum surface 62, and plantar surface 61 up to the inner ankle 63 was constructed. The test fixture allowed for very precise, repeatable measurements of flux density from the hallux (position=0 mm) to the inner ankle (position=150 mm) and beyond, and at a penetration depth of 10 mm from both the plantar 61 and dorsum 62 surfaces.

The coils 13 were selectively and collectively energized, and the results are shown in graph FIG. 9A and table 9B. (These show the same, identical information.) "Coil 1" 91 through "Coil 6" 96 show each individual coil being individually energized. "All Coils" 90 and "All 6 Coils Concurrently Energized" show all coils energized at the same time.

For the entire forefoot, flux density was extremely uniform 90, coherent, and with greater strength than any of the individual coils 91-96 (FIG. 9A and FIG. 9B). Penetration into the foot was deeper than necessary (typically >25 mm) and coverage was identical along both the plantar and dorsum surfaces.

Most importantly, the present invention can achieve dosage levels that rival a high-power MPTD. Because the entire foot is concurrently treated 90, the entire foot can receive a consistent and uniform daily dosage of 500 $\Sigma\Delta Br$ to 2,500 $\Sigma\Delta B_T$ in 10 to 55 minutes.

When the test fixture was operated continually for a very long time, thermal imaging revealed no temperature increase whatsoever. The use of a multiplicity of axially aligned low voltage coils to form a solenoid also solves the problem of thermal runaway.

No known MPTD can safely treat an entire foot concurrently and this uniformly such as this test demonstrated is possible.

The Applicator

Because of the need to axially align a multiplicity of coils 13 to form an operative solenoid 15 and then position the foot 11 within the core of the solenoid 15 the applicator design is even more integral to MPTD of this invention than with most MPTDs.

The applicator 10 of the current invention allows a patient to simply slide their foot 11 into it (FIG. 1). There are no straps or adjustments, there are no moving parts at all, there is no need to reposition the foot, one-size-fits-all, and the entirety of the foot is concurrently treated from the hallux (big toe) 67 to the heel 68, and up to the ankle 69 (FIG. 6B). At any time, the patient may withdraw the foot. Because the low voltage coil arrangement generates no heat there is no risk of thermal injury and there is no ice chest or liquid cooling.

The preferred applicator's interior is shaped like a hi-top sneaker, a chukka boot, or a desert boot except that the back (heel) area 14, 68 is entirely open, similar to an open-back boot (FIG. 3A and FIG. 5A). The toe area 12, 67 is open to aid cleaning and for comfort. It has an interior ("treatment zone") that extends from the hallux (big toe) 67 to the heel 67 and up to the inner ankle 63 (FIG. 6A).

The foot may be slid into the applicator 10 easily. When inserting the foot either the foot's dorsum surface 62 or the inner ankle 63 will stop at the applicator's interior upper surface 64 (FIG. 6A). At this point the foot has been perfectly centered and perfectly aligned. In this position, all three of the important treatment areas that are rich in nerve endings are in close proximity to the coils 13: the plantar surface 61, the dorsum surface 62, and the inner ankle 63 (FIG. 6B). The simple act of inserting a foot until it stops is sufficient to ensure a consistent, repeatable, near perfect alignment within the applicator 10.

The applicator can be configured to only treat the forefoot. In this configuration the proximal half 12 of the applicator is eliminated. All principles and benefits of the current invention apply equally to the forefoot configuration.

The applicator can be optimized for treating the hand. This configuration is similar to the forefoot-only version except that the height of the applicator's interior treatment chamber is reduced to more closely conform to that of a hand. All principles and benefits of the current invention apply equally to the hand configuration.

Removal of the foot (or hand) is as simple as just pulling it out. There are no straps, no closures, no adjustments, no moving parts at all The Coils & Solenoid The exterior of the applicator 10 positions, retains, and forms the coils 13 into an axial alignment (FIG. 1 and FIG. 6B and FIG. 7A and FIG. 7B). The axially-aligned coils 13 start at the distal end 12. Successive coils progress to the proximal end 14 of the applicator 10. The axially-aligned coils 13 are positioned sufficiently close to each other, and have similar enough shape to each other that they form an operative solenoid 15 (FIG. 7A and FIG. 7B and evidenced 90 by FIG. 9A and FIG. 9B). As flux is most dense closest to the coils, close positioning of the coils to the foot is beneficial (but not critical) for proper operation (FIG. 6A).

The number of coils is flexible; more coils result in greater flux density (strength) and fewer coils is more economical. FIG. 7A shows an applicator 10 with 22 total coils 13 (11 of which encircle the forefoot) and FIG. 7B shows an applicator with 14 total coils 13 (7 of which encircle the forefoot). The lengths of each coil can be varied; when wound shorter they will concentrate their power, and when wound longer they will spread their flux out evenly across their width.

Typically, a section of the applicator such as the forefoot will be about 150 mm in length and with 7 coils each will therefore be about 20 mm in length. (Math: 150 mm=7 coils≅20 mm).

Along the distal (forefoot) portion of the applicator 12, coils will preferably have a larger circumference as they stack (or sequence) further from the distal end 12. As a result, the coils with larger circumferences will have less flux density. This can be compensated for my making the coils progressively shorter as they get further from the distal end 12. Another way of compensating is to use a larger diameter wire (smaller AWG) which will allow more turns and more current and produce higher flux density. However, this is actually not preferred because maintaining higher flux density at the nerve endings in the toes 67 can be beneficial and the nerve rich inner ankle 63 already has many coils passing nearby from the proximal end 14 of the applicator 10.

The applicator's distal portion 12 has horizontal stair-stepped shelves that the coils are wound onto (FIG. 6A). These stair-stepped shelves 66 keep the coils 13 in position; without them the coils would be inclined to slide down the inclined surface that is contoured to the dorsum surface 62.

On the bottom of the applicator 65 are stand-off-like supports so that any weight placed on the bottom of the applicator will transfer to the surface below without crushing the coils 13 or causing insulation to wear through (FIG. 6A and FIG. 6B). A drawing showing the coils 13 and their relationship to the stair-stepped shelves 66 and bottom stand-off supports is FIG. 6B.

At the applicator's proximal end 14 the coils follow a modified path (FIG. 6B and FIG. 7B). These proximal coils pass under the bottom of the foot (plantar surface) 61 and then vertically pass over or near the ankle 69 and then they form around the inner ankle 63, and back to near the ankle on the opposite side and then vertically return to the bottom of the foot 61, as schematically illustrated in FIG. 6B. "U" shaped clips 18 are molded into the applicator above or near the ankle to facilitate the transition of the coil 13 through the necessary turn from vertical to horizontal. These clips 18 are clearly illustrated in FIG. 1 and FIG. 7B. The proximal coils all pass around the inner ankle 63; this is beneficial because large and important nerve bundles also pass through this area and thus, they get a little "extra" treatment.

In practice, it has been found to be best if the applicator assembly 10 consisted of two halves: one for the distal end and one for the proximal end. These two halves can snap together or can be screwed together.

The Housing

The applicator 10 is housed within a small enclosure 24 that encloses the applicator 10, the coils 13, and most of the electronics (FIG. 3A and FIG. 3B), thereby eliminating the heavy interconnecting cable. The entirety of the MPTD fits in a 6"×6"×12" housing (except for the small external power pack.)

The housing 24 is preferably built as a distal/proximal clamshell. In this way the two halves of the applicator are also clamped together. Alignment of the clamshell and applicator 10 is accomplished via studs, lugs, or beams molded into the plastic that the applicator halves are comprised of. This also eliminates much of the need for fasteners. Flanges may be added to the applicator to attach to and secure the outer housing; one such mounting flange is shown near the inner ankle of the applicator in FIG. 1, 19.

Both Feet Concurrently

The ability to treat both feet concurrently is especially appealing. This can be accomplished using the present invention in two ways:

1) Two single-foot applicators can be used (FIG. 2). The two applicators 20, 21 can be positioned at whatever distance and angle the patient finds to be most comfortable. The other benefit is that each such applicator can have its own power pack, and for medical grade power packs two smaller ones can be cheaper than a larger one with double the output. Regulatory compliance under IEC 60601 can also be simpler.

Even though the housings are separate 20, 21, the two applicators function as one MPTD. The two separately housed applicators can communicate using Bluetooth, with one applicator 20 being the primary the other 21 being secondary. The secondary applicator 21 does not need a display or button as it will receive operating parameters via Bluetooth from the primary unit. In the preferred embodiment a Raspberry "Pico W" CPU which has built-in Bluetooth is used.

2) The second way is to place two applicators 10 within a single housing 50 (FIG. 5A and FIG. 5B). In a clinical environment this can be advantageous as it is simpler for patients to understand and if there are multiple treatment bays, each would have a single physical device.

Another advantage of two applicators 10 within a single housing 50 is that the coils 13 from both applicators can be wired in series or parallel 121 and share the same electronics board (FIG. 12). Shared electronics offers some economy, albeit the power is split. The decision whether each applicator within a housing is wired to its own electronics board or whether they share an electronics board is a price/performance tradeoff. Either configuration takes advantage of the principles and benefits of the present invention.

Recap

As can now be seen, a multiplicity of axially aligned coils 13 form a large volume of Core Flux within an applicator 10 that self-aligns a foot and can deliver a sufficiently large dosage of magnetic pulses 90 to an entire foot (or to both feet) to achieve clinical levels of medical efficacy for pain relief within a reasonable amount of time.

This novel approach solves the long felt need of a simple, effective way to relieve pain using magnetic pulses that can be self-administered safely and reliably in an in-home or clinical setting.

DETAILED DESCRIPTION

Figure 1:
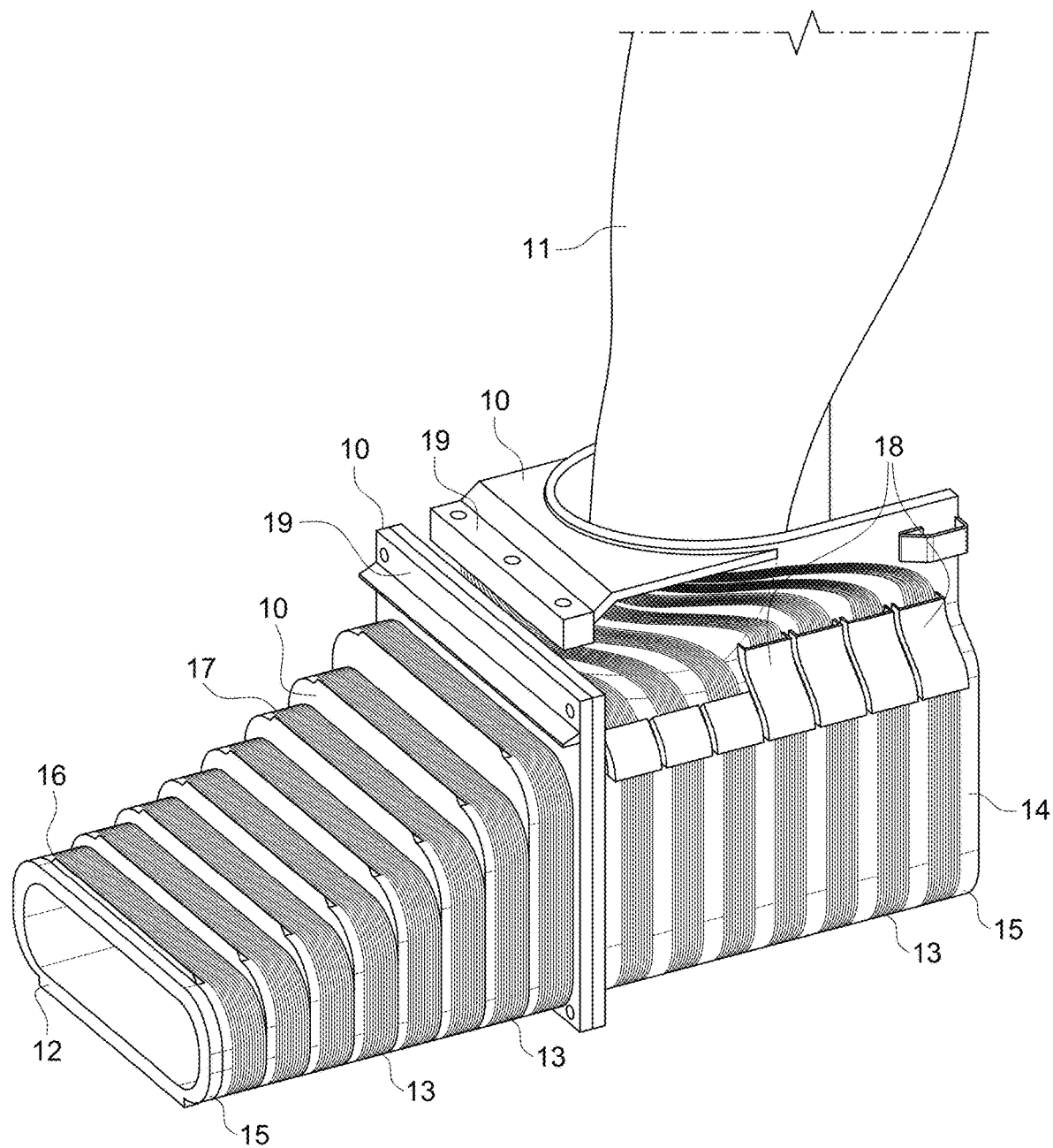
FIG. 1 is a perspective view of the invention with a foot 11 inserted into the Magnetic Pulse Therapy Device (MPTD) that has had the housing (not shown) removed. This illustrates the preferred embodiment wherein the distal end (toe end) 12 of the device has eight coils 13 and the heel portion 14 of the device has seven coils 13, for a total of 15 coils. The coils are wound around the applicator's structure 10 which forms the solenoid's air coil 15.
Figure 2:
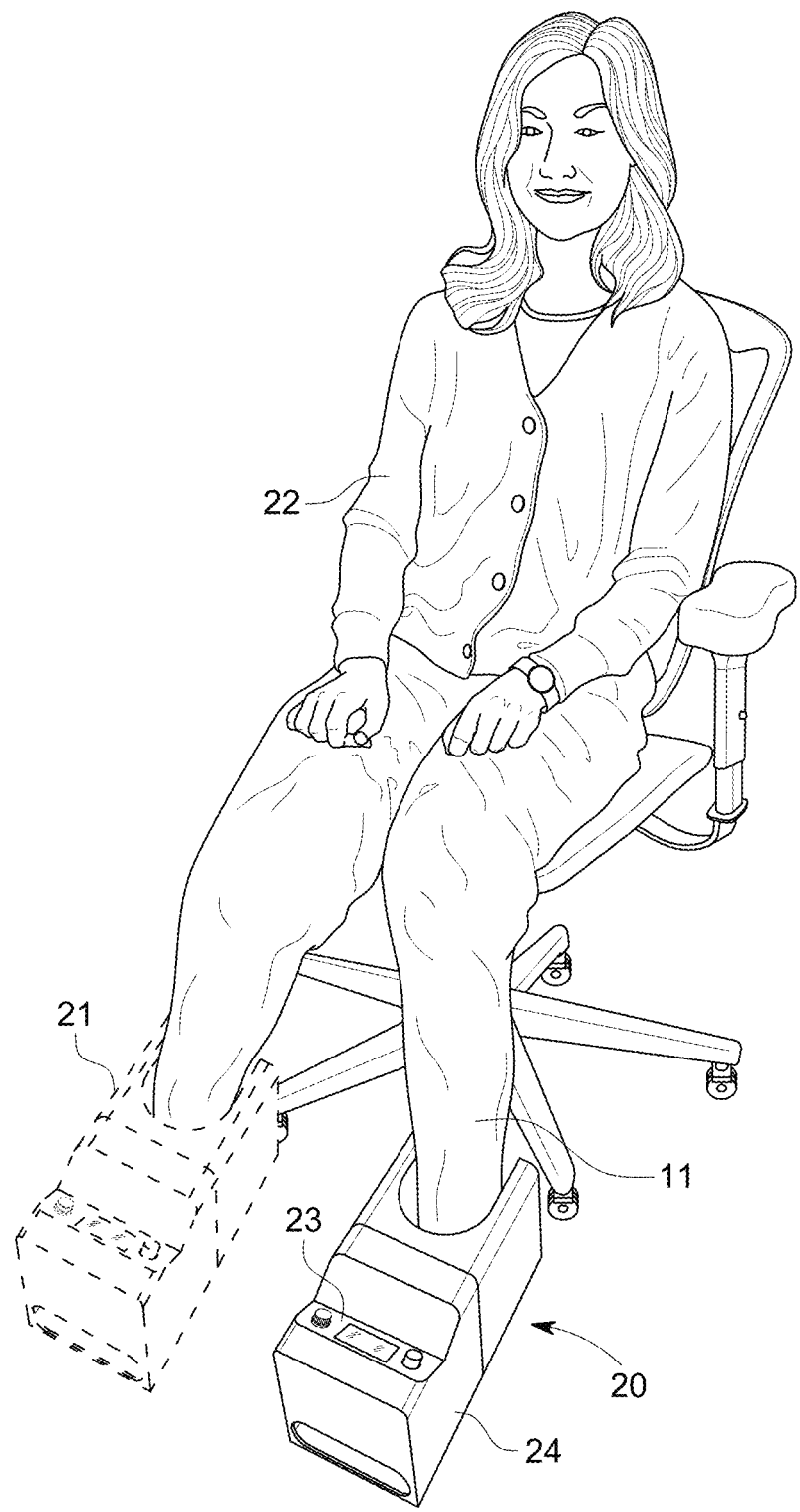
FIG. 2 shows the MPTD 20 with a patient's left foot 11 inserted. Also shown is a second (optional) MPTD 21 that could be on the patient's other (right) foot. The patient 22 is shown seated during treatment.
Figure 3A:
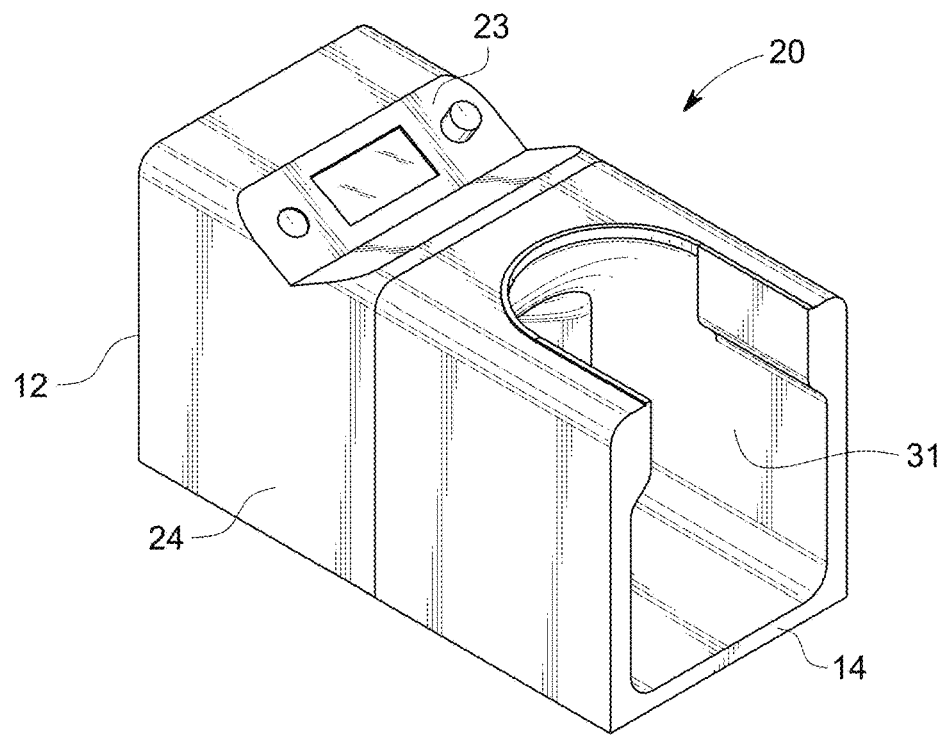
FIG. 3A shows the MPTD from the perspective of the proximal (heel) end 14 of the device. The opening 31 wherein the foot may be inserted through the housing and into the applicator is apparent.
Figure 3B:
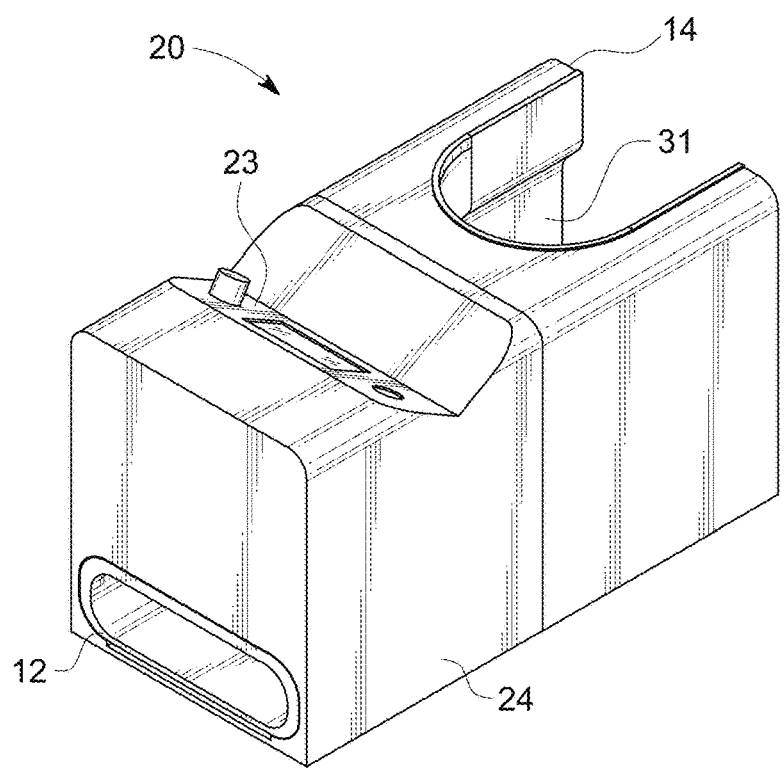
FIG. 3B shows the same device shown in FIG. 3A from the perspective of the distal (hallux/toe) end 12 of the device. An opening for the toes and for cleaning is illustrated 12.
Figure 6A:
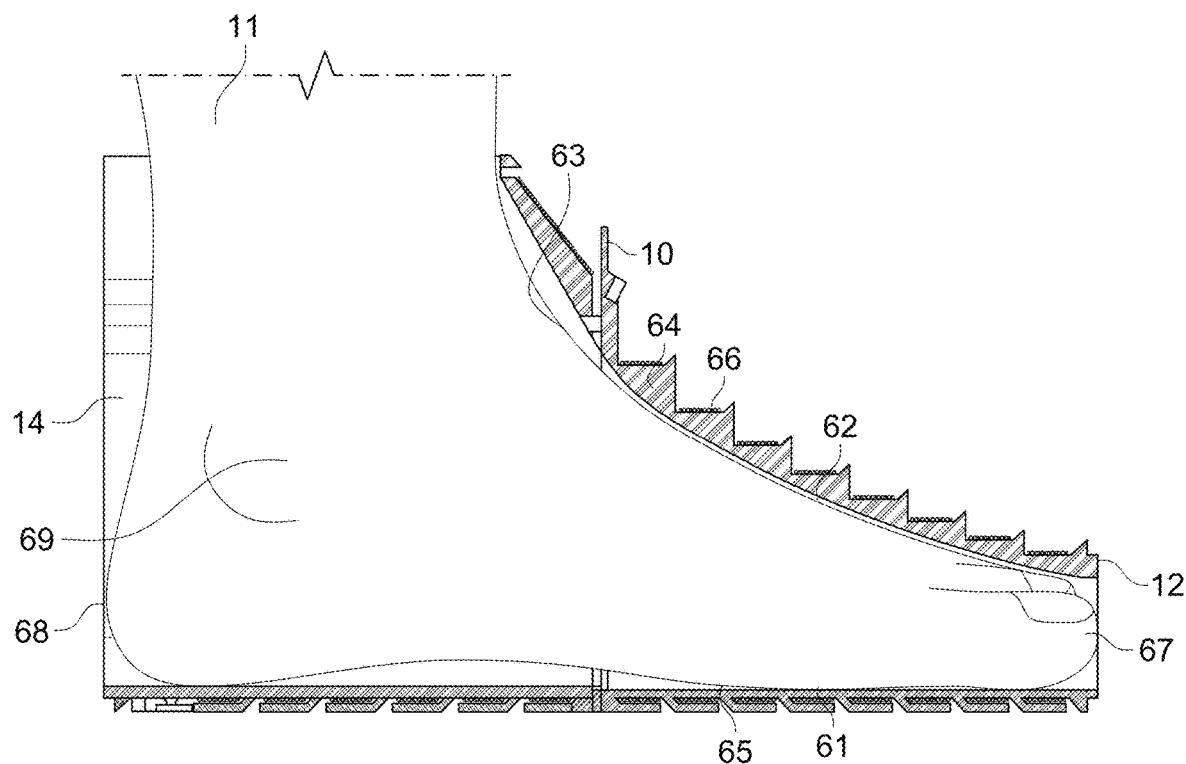
FIG. 6A is a cross section of the applicator 10 showing the foot 11 fully inserted. The back (left side) 14 is open to facilitate entry. The plantar (bottom) surface 61 and dorsum (top) 62 surface and inner ankle 63 of the foot all are in close proximity to the applicator's top 64 and bottom 65 surfaces. The stair-stepped shelves 66 which support the coils are above the dorsum 62 surface.
Figure 6B:
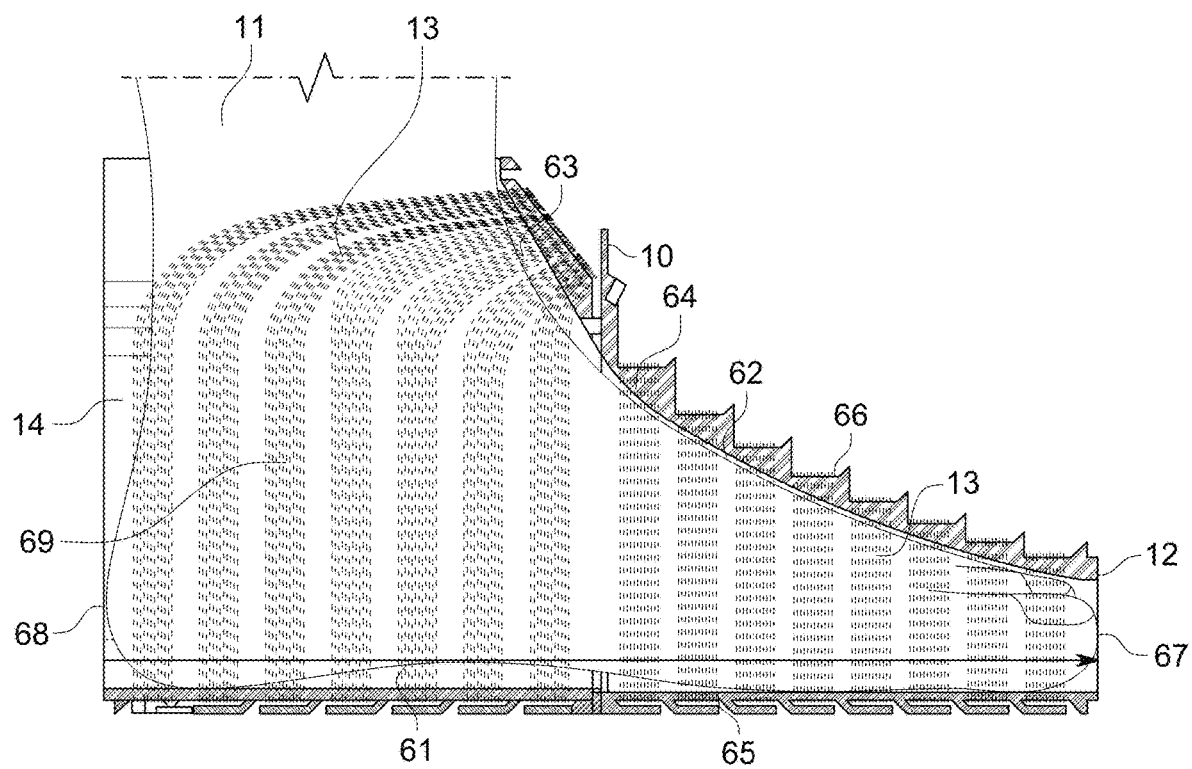
FIG. 6B shows the same cross section as FIG. 6A with the addition of showing as dotted lines the optimal positions of the coils 13. These coils would be the same on the back side of the applicator and in the cut-away portion. The coil count matches the preferred embodiment of 8 coils encircling the dorsum surface 62 and 7 coils on the proximal end 14.
Figure 10:
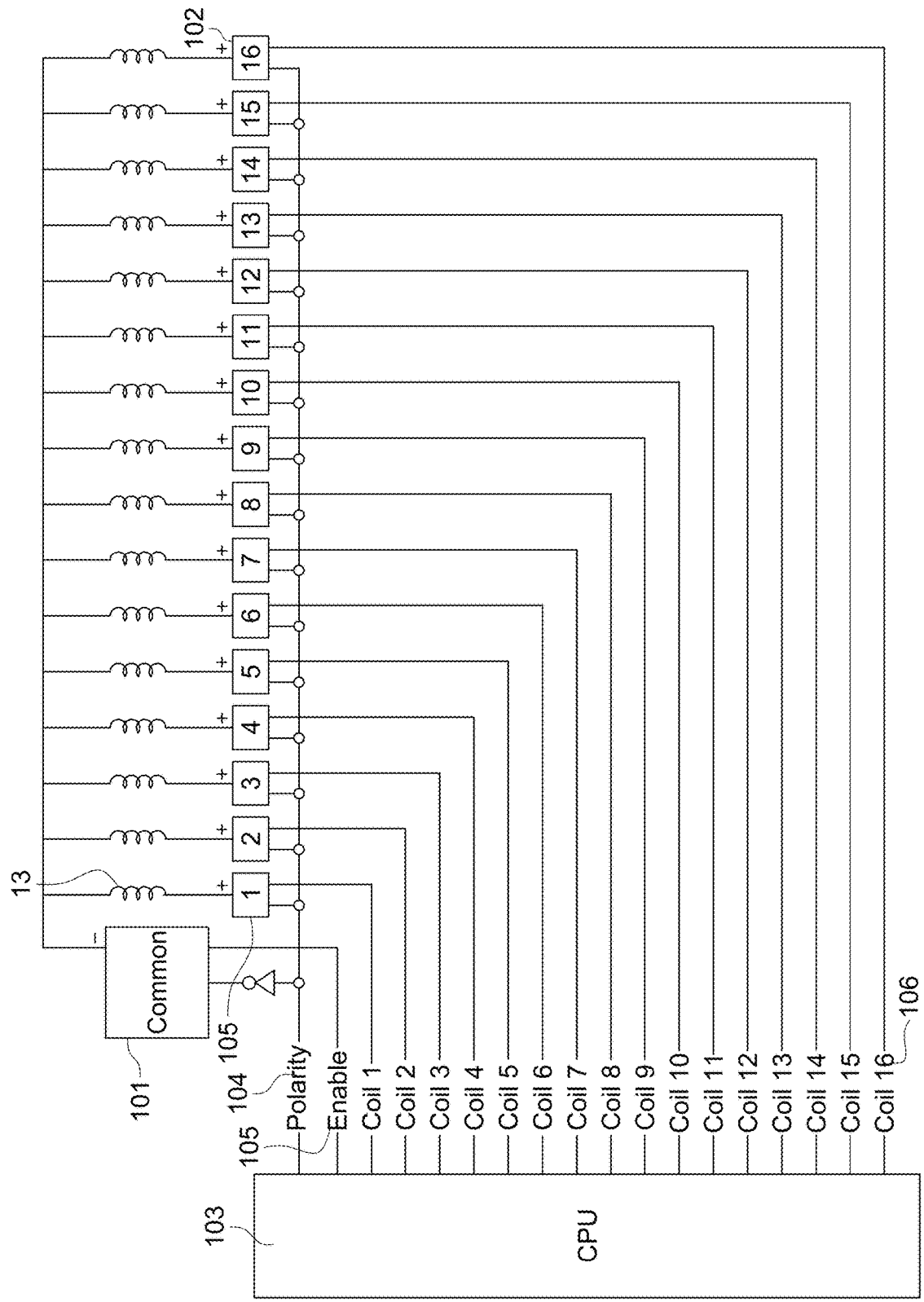
FIG. 10 is an electrical schematic showing the connection of a 16-coil system wherein all 16 coils share a common bridge (aka "driver") 101. Each of the 16 coils are individually controllable by their respective bridge circuits 102 (boxes 1 to 16) under control of the CPU. The "Polarity" line 104 controls the output polarity of the bridge circuits 105 as indicated by the "+" and the "Common" driver 101 inherently has opposite polarity as indicated by the "−". The "Enable" line 105 enables the selected circuits for the duration of the enable pulse.

The present invention is a Magnetic Pulse Therapy Device (MPTD) designed to provide therapeutic pulses to an appendage such as a foot 11 (FIG. 1 and FIG. 2). This is accomplished through a multiplicity of axially aligned coils 13 (FIG. 11) that are wound onto an applicator 10 (FIG. 7A and FIG. 7B) which contacts both the plantar (bottom) surface of the foot 61 and either the foot's dorsum (top) surface 62 or median (inner) ankle 63 (FIG. 6A). The coils encircle the inserted appendage 11 (FIG. 6B). The coils are connected to and are energized by a series of half bridges 102 (herein simply called "bridges") (FIG. 10, FIG. 11, FIG. 12) each as shown 102 in FIG. 13 and which are operably connected to a microcontroller (CPU) 103. The coils 13, applicator 10, and electronics (not shown but located above the dorsum of the foot) are contained within the housing 20, 50 (FIG. 3A and FIG. 3B).

Figure 4:
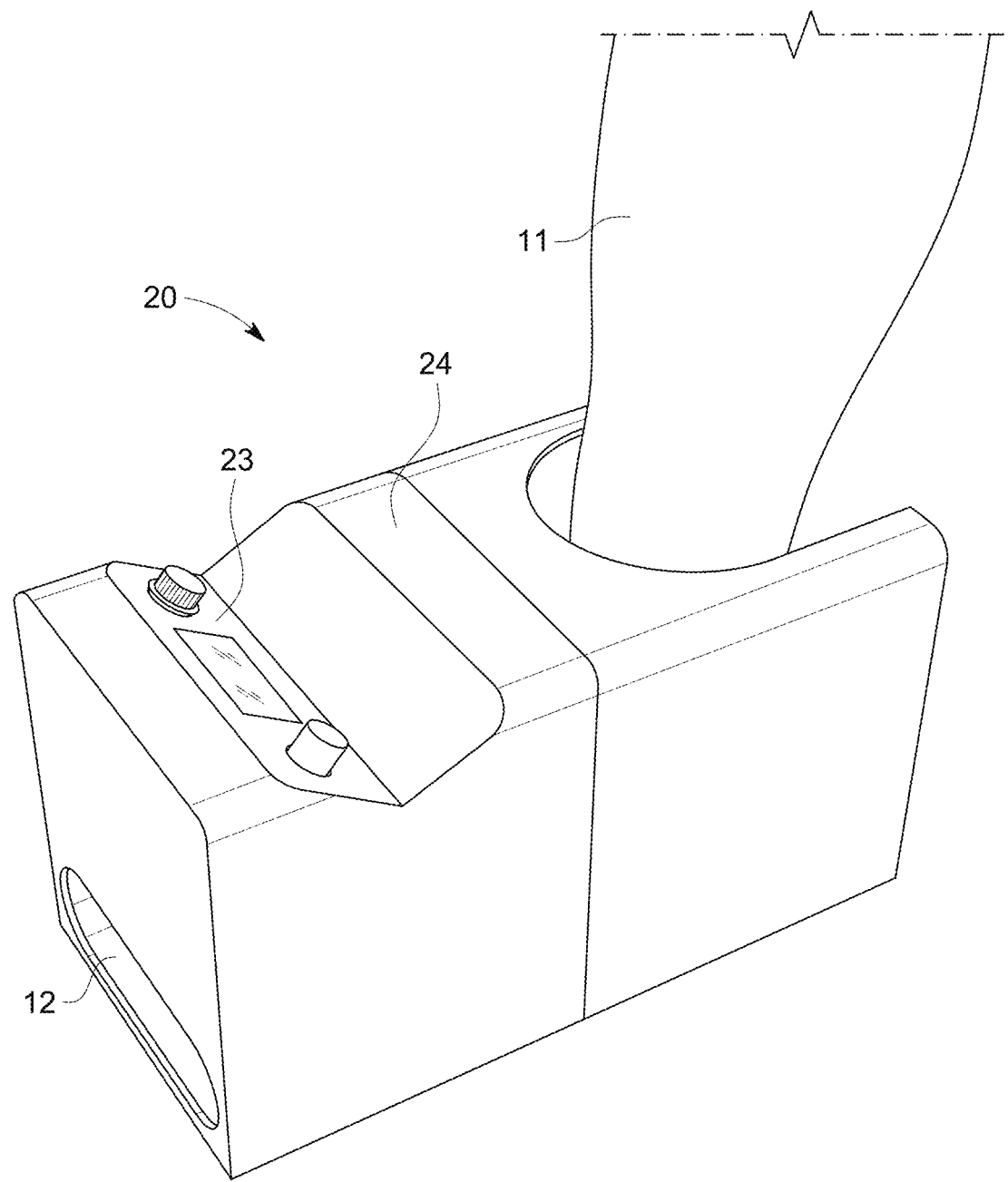
FIG. 4 shows the MPTD with the patient's foot 11 inserted. Also shown is a display and control knob 23 by which the device could be operated.

The patient's foot 11 is inserted distally (toes-first) into the applicator 10 from the proximal (heel) end 14 (FIG. 3A) until it makes contact with either the dorsum surface 62 or the median ankle 63 (FIG. 6A). It does not matter which surface of the foot first makes contact with the applicator 10. Either way, when fully inserted (FIG. 4) the foot will be in contact with the applicator along two surfaces: the bottom 65 and the top 64 and will resemble FIG. 6A. In this position the ankle 63, 69 will have been automatically centered side-to-side by the curvature of the applicator's opening 31 at the inner ankle 63. The foot may at any time be immediately removed by simply pulling it out; there are no straps or retainers.

The preferred embodiment of the applicator 10 is shown with the housing removed and a foot 11 inserted in FIG. 1.

The preferred embodiment has eight coils along the distal (dorsum) end 12 and seven coils along the proximal (heel) end 14, for a total of 15 coils. Alternative embodiments may have any number of coils (three or more) as needed to achieve the desired field strength.

The MPTD may alternatively be arranged with two (or more) applicators 10 in a single housing 50 (FIG. 5A and FIG. 5B) or in separate housings 24 (FIG. 2) to concurrently treat both feet. The underlying principles of the current invention are the same for any such configuration.

The MPTD is equally applicable to treating the hands and other parts of appendages such as a segment of an arm or leg that is inserted into the core of the solenoid 15.

The Applicator & Windings

A cross section of the applicator is shown in FIG. 6A. The proximal end 14 of the applicator (the left side in FIG. 6A) is entirely open (FIG. 3A), allowing unrestricted ingress and egress of the foot 11. The bottom of the applicator 65 is generally flat and the top surface of the applicator 64 is preferably contoured similarly to a typical foot's dorsum 62, curving up from the toes 67 to a typical median (inner) ankle 63 as shown in FIG. 6A. Generally, the width and height of the top surface will be sufficient to accommodate the largest size foot desired, typically a US shoe size 13 which represents the 95th percentile. It is not critical that the applicator be perfectly shaped or sized or be tight to the foot to be functional.

The coils 13 are wound to encircle the applicator 10, and therefore also the foot 11 (FIG. 6B). When inserted, the foot 11 will necessarily be in close proximity with the coils 13 (FIG. 1 and FIG. 6A), and the coils 13 will encircle the foot 11 (FIG. 1 and FIG. 6B). An important aspect of the current invention is that because the foot 11 is encircled by the multiplicity of coils 13 it is within the core of the operative solenoid 15 and is therefore treated primarily by Core Flux.

The exterior of the applicator 10 has a series of tiers, or stair-stepped shelves 66 above the dorsum (top) surface 64 (FIG. 6A). The stair-stepped shelves 66 prevent the coils from sliding down towards the toe 67 as would happen if the top surface 64 lacked these stair-stepped shelves or some other retainer. It is preferable that the stair-stepped shelves 66 not be very wide, so that the coils 13 remain in close proximity to the foot's dorsum surface 62; more stair-stepped shelves 66 can better follow the contour of the dorsum surface 62. The preferred embodiment with eight stair-stepped shelves 66 works well (FIG. 1). The bottom exterior of the applicator may also have guides 65 or channels which may support the applicator on the bottom so that the foot does not crush the coils 13 passing underneath (FIG. 6A).

Figures 9A, 9B:
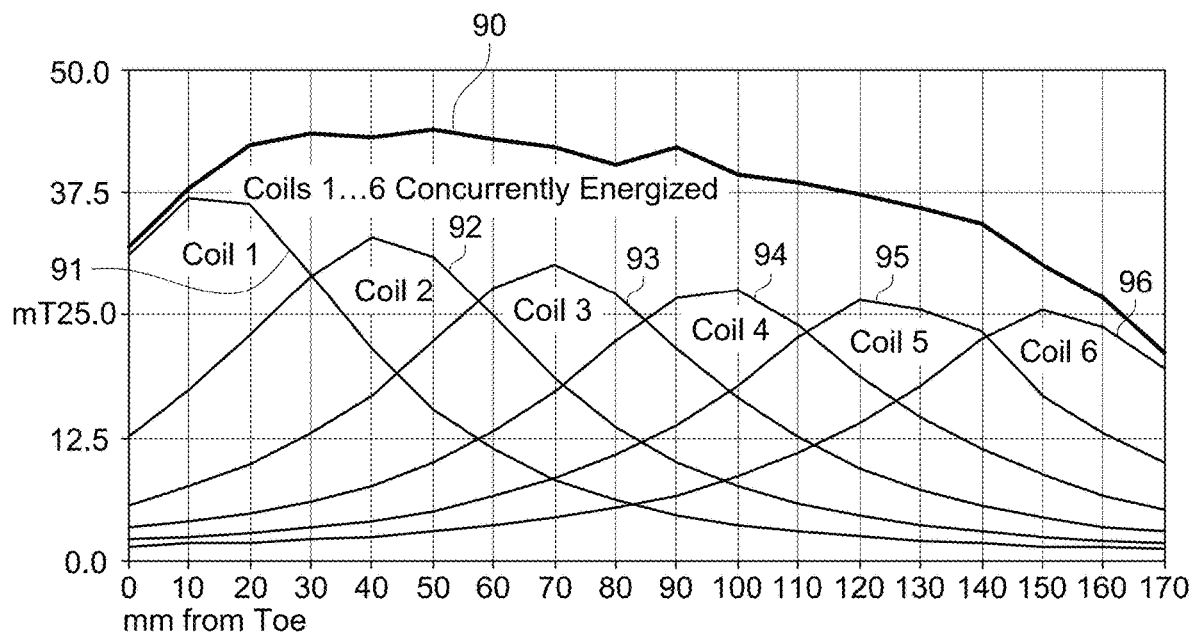
FIG. 9A is a graph showing field measurements of magnetic flux density of a 6 coil 150 mm long forefoot shaped test fixture. Each of the six graph lines ("Coil 1" 91 through "Coil 6" 96) show the flux density recorded in 10 mm increments (from distal 12 to proximal end 14) for each of the six axially aligned coils, with Coil 1 being located closest to the toes 16 and Coil 6 being located closest to the inner ankle 17. The graph line labeled "All 6 Coils Concurrently Energized" 90 shows the flux density recorded in 10 mm increments (from the distal/hallux/toe end) when all six of the coils are concurrently energized. All measurements are in milli-Tesla (mT.) The chart extends to 170 mm even though the fixture was only 150 mm because measurements were taken beyond the end of the test fixture. Most notable is that with All Coils 90, a flux entity of 35 mT+15% is delivered from toe to inner-ankle.
FIG. 9B is the table of field measurements that are displayed in the chart depicted in FIG. 9A. Values are in milli-Tesla (mT).

While it is convenient that the number of stair-stepped shelves 66 match the number of coils 13, there is no requirement that this be so, and coils 13 may be wound across multiple stair-stepped shelves 66 or multiple coils 13 can be wound on a single shelf 66. A coil length of 15 mm to 20 mm has been found to be convenient in the preferred embodiment. In an alternative embodiment the number of coils 13 may be different and thus an appropriate coil length would be the length of the distal portion 12 of the applicator 10 (about 150 mm) divided by the desired number of coils 10. Eight coils are shown for the dorsum in FIG. 6B and FIG. 1, eleven dorsum coils in FIG. 7A, FIG. 7B, and six were used for the test Fixture in FIG. 9A and FIG. 9B.

Once all coils 10 are wound, they are connected to the electronics (not shown) which are stowed above the dorsum portion 12 of the applicator 10. The applicator 10 with its coils 13, and the electronics then slide into and are enveloped by the outer housing 24, 50 (FIG. 3A and FIG. 3B).

Figure 7A:
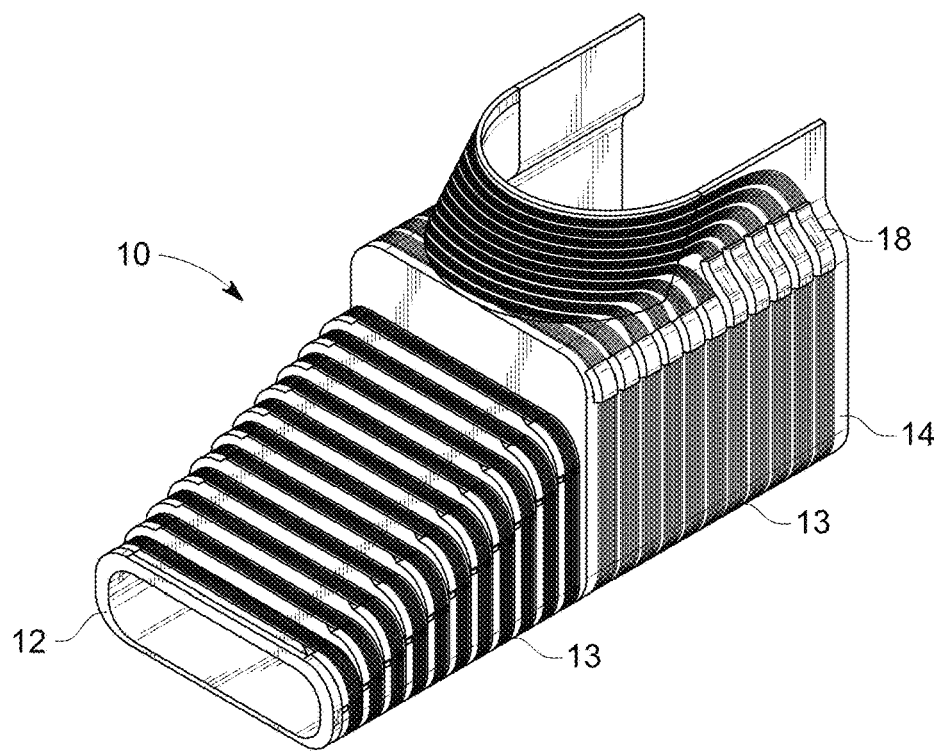
FIG. 7A is a perspective view of the applicator assembly 10 configured to have eleven coils along the distal (hallux/toe) end 12 and eleven coils along the proximal (heel) 14 portions of the applicator structure 10. The overall size of the applicator is the same as shown in FIG. 7B and elsewhere.
Figure 7B:
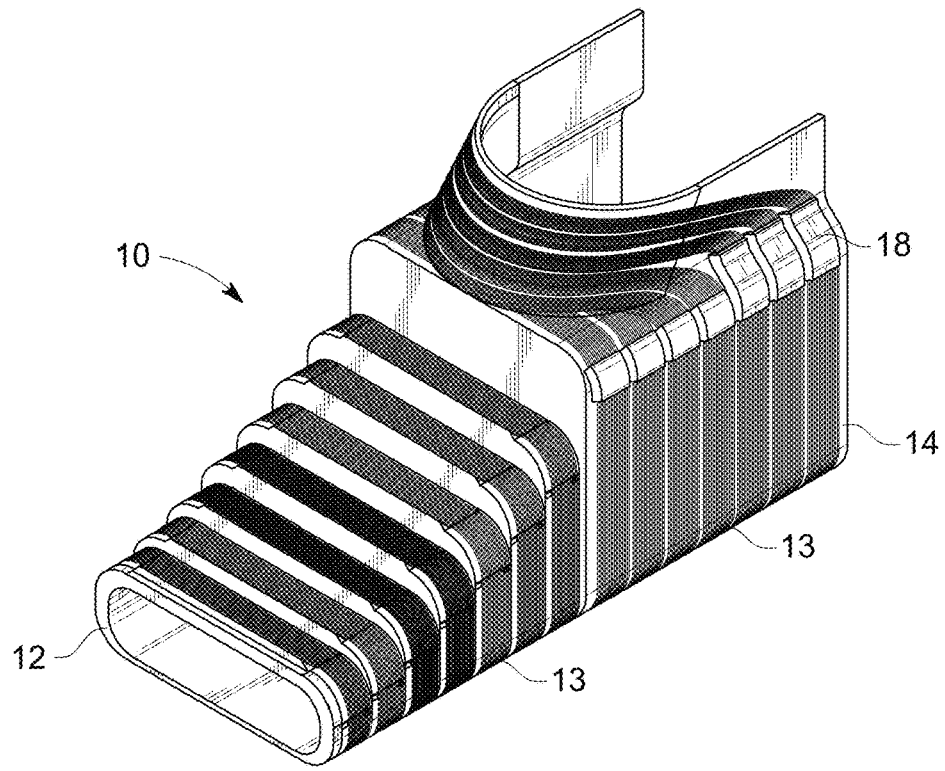
FIG. 7B is a perspective view of the applicator assembly configured to have seven coils along the distal (hallux/toe) 12 end and seven coils along the proximal (heel) portions 14 of the applicator structure. The overall size of the applicator is the same as shown in FIG. 7B and elsewhere.

If there are proximal coils 13, they are similarly wound except that they pass near or over the ankle 69 and then around and in front of the inner ankle 63 and back to the opposite ankle 69 and then under the plantar surface 61 (FIG. 6B and FIG. 7A and FIG. 7B).

The Solenoid and Core Flux

For optimal performance it is important that all of the coils 13 somewhat close and are approximately axially aligned. As much as possible, each of the coils should have approximately the same circumferential profile, particularly along the bottom 65 and sides. The coils 13 will, of course, be roughly parallel to each other but not entirely aligned along the top because of the stair-stepped shelves 66.

All of the coils 13 must be energized with the same "logical" rotation so that the flux from each coil has the same polarity. (A "logical" rotation in a multi-tap configuration means that adjacent coils 13 will have their connecting leads reversed or else they will be physically wound in the opposite direction from each coil's 13 neighbors so that all coils 13 produce magnetic flux with the same polarity.) In this way, the Core Flux from each individual coil 13 will merge with the Core Flux from neighboring coils 13 to form a single operative solenoid. Due to the high field coherence and field coherence length inherent in Core Flux the multiplicity of close by and axially aligned coils 13 will form a single ("operative") solenoid 15 and this solenoid 15 will form Core Flux from toe 67 to ankle 63 or heel 69.

To establish that an operative solenoid exists and Core Flux has formed (as intended for the purposes of this invention) all coils 13 in the solenoid would be energized concurrently. Then, field strength measurements would be taken along the length of the solenoid 15. These field strengths then can be graphed and visualized, such as was done in FIG. 9A. The fewer "valleys" that exist in the graph between the coils 13, the higher the quality of the Core Flux and the more uniform the field is within the core of the solenoid 15. As the coils separate, or as the circumferences of the coils 13 become too dissimilar, or as the current through the coils 13 is inadequate then the solenoid becomes increasingly defective and valleys will form in the graph. It is not important whether there is an upward or downward overall trend, especially at the center points of the coils 13; it is deepening valleys between the coils 13 that indicate an increasingly defective solenoid. At some point, perhaps when the field strength between coils 13 only 50% of the center of the coils 13, one could conclude that the solenoid 15 is becoming non-functional, although this threshold would be somewhat contextual with the applicator's functioning.

BEST MODE FOR CARRYING OUT THE INVENTION

The following is a description of how to construct the preferred embodiment of the invention. The level of detail provided is intended to be sufficient for a person "skilled in the art" to build a working device. The skills needed are 3D (Computer Aided Drawing) CAD and 3D printing for creating the applicator 10, basic wiring for creating the coils 13, electrical engineering for the electronics, CAD and 3D printing for the housing, and some minimal ability to program a microcontroller CPU.

1) Create an Applicator:

Create the interior of the applicator 10 by scanning a large human foot 11. In a CAD system, create a lateral cross section of the scanned foot along the hallux 67 to tuberosity of the calcaneus (large toe to heel 68 center) line and discard the rest of the scan. Extrude this cross section left to right to form the desired width of the applicator 10 interior, generally 120 mm. Extrude the toe 67 portion beyond the distal 12 end of the applicator and then truncate it, to create an opening. Extend the proximal surface 14 (back of the heel 68 and ankle) beyond the length of the applicator and then truncate it at the proximal (heel) end 14. Extrude the plantar (bottom) surface 61 beyond the floor of the applicator 10 and truncate it at the applicator's desired floor 65. Add sides and contour to the top and bottom. At this point the CAD should have an inner shell with the distal 12 and proximal 14 ends open. Scale the shell up from the bottom of the applicator 65 to allow for different foot sizes and shapes, a scaling factor of +3% to +5% has proved well. Truncate the distal 12, proximal 14 and top of the shell to fit the desired applicator's 10 maximum size.

Along the dorsum surface 64 construct stair-stepped shelves 66 to support the coils 13; in the preferred embodiment there will be eight stair-stepped shelves 66 (FIG. 6A). Add slots or supports under the plantar surface 65 to support the weight of the foot and allow the wires to pass under (FIG. 6B). Add clips or hooks 18 near the heel so that the wires extend vertically from the bottom 65 to the heel 68, then around the inner ankle 63. The preferred embodiment is illustrated in FIG. 1 and has eight coils on the distal (dorsum) half 12 and seven coils around the proximal half (heel portion) 14 of the applicator 10 (FIG. 1, and FIG. 6B).

Add the retaining clips 18 shown in FIG. 1 so that at or above the heel 69 the coil 13 wires can bend towards the inner ankle 63. Add whatever mounting flanges 19 or holes are desired for attaching the applicator 10 shell to the housing 24 and for attaching the printed circuit board for the electronics above the dorsum 64. The applicator in the CAD system will look like FIG. 1.

Export the CAD file and print it using a 3D printer. The recommended 3D printing orientation is with the proximal 14 end of the applicator 10 portion(s) on the build plate.

2) Create the Coils:

The number of coils 13 needed primarily depends upon the power desired for the device. More coils 13 are more power in a linear relationship. The preferred embodiment has 15 coils, with 8 in the distal portion 12 of the applicator 10 and 7 in the proximal portion 14 (FIG. 1 and FIG. 6B).

Create the coils 13 from #20 AWG magnet wire. On the distal end 12, wrap the coils 13 as indicated in FIG. 6B. On the distal end 12 the wires for each coil 13 will wrap under the plantar surface 65, and onto the stair-stepped shelves 66 above the dorsum surface 64. On the proximal end 14 the wires will wrap under the plantar surface 65, then vertically up to the clips 18 near the heel 69, around the inner ankle 63, to the clips 18 on the opposite side, and vertically back under the plantar surface 65. Make 32 turns (wraps) on each coil 13. (The number of wraps can be optimized, but this is not essential to do this for operation.) The finished result should look similar to FIG. 1 and FIG. 6B.

3) Build the Electronics:

A total of 16 bridges 102 are required for a 15 coil 13 device. Do not install coil 16 or else electricity will back-feed if coils are selectively operated. (If all coils 13 will be only energized concurrently then coil 16 may be added.) The BTS7960B is a reasonable choice for the bridges, although many suitable alternatives exist.

Figure 11:
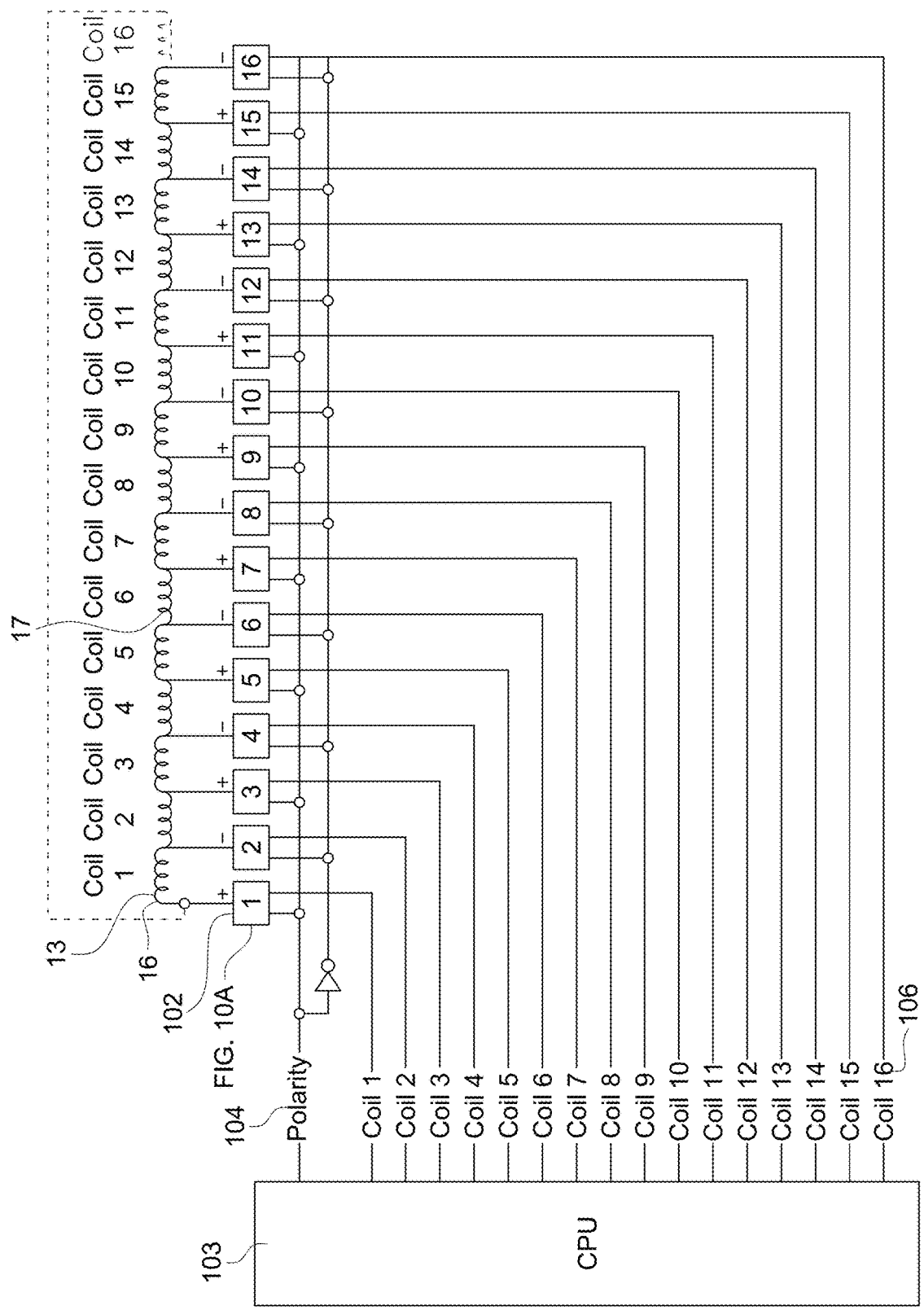
FIG. 11 is the schematic for the preferred embodiment, which has 15 coils. This coil configuration is called "multi-tap" because the connection of the coils resembles a multi-tap transformer. Odd numbered coils 16, 102 (Coil 1, Coil 3, Coil 5, etc.) are shown wound in the opposite direction from even numbered coils 17, 102 (Coil 2, Coil 4, Coil 6, etc.) by the reversed spiral. Odd numbered (boxes 1, 3, 5, etc.) bridges ("drivers") inherently have the opposite polarity of even numbered (boxes 2, 4, 6 etc.) bridges by virtue of the NOT gate. The alternating polarities of the bridges in conjunction with the alternating direction of the coil windings ensures that the magnetic polarity of all axially-aligned coils is the same. Important: Coil 16 is drawn in a dotted line to illustrate that it is not provided, (and must not be).

Connect the coils 13 to the bridges 102 as indicated in FIG. 11, noting that this schematic uses a multi-tap solenoid configuration and therefore even numbered coils 17 will be connected with reversed polarity and as illustrated in FIG. 11. This is necessary so that the flux polarity on all coils is in the same direction and is additive.

The INH control lines 106 for the bridges 102 are logic level compatible and can wire directly to the CPU's 103 GPIO lines (FIG. 11). In the preferred embodiment, it is desired that individual coils 13 may be selectively operated and therefore each bridge 102 should connect to a GPIO dedicated to that bridge 102 so that they may be independently controlled. If independent control is not desired, then all INH lines 106 can be connected together and use a single GPIO line, but if this is done it is recommended that a buffer re-drive this signal so that the GPIO is not overloaded.

Connect the IN lines 104 for all odd numbered bridges together and then to the CPU's GPIO assigned to control polarity (FIG. 11). Connect the IN lines for all even numbered bridges to the output of a NOT gate and then the input of this gate to the Polarity line 104 (FIG. 11). This ensures that adjacent bridges 102 always have opposite polarity.

Use a 24 VDC power supply such as Mean Well GSM90A24 medical grade power supply which is rated at 90 watts. The output of this power supply connects to a constant current ("cc") regulator set to 3 amps. The output of the current regulator connects to a 30 mF capacitor. The capacitor connects to the high side of all of the bridges 104, indicated as "VS" in FIG. 13.

4) The CPU & Software

For the CPU 103, a Raspberry RP2040 CPU is preferred as it has many IO lines and built-in PIO capabilities with DMA support, allowing for complex and precise pulse timing.

CPU 103 GPIO lines control the polarity (IN) 104 and GPIO lines enable the bridges through the INH lines (FIG. 11). The CPU is fast enough that pulse timing can be done through timing loops but more preferably is done through the RP2040's PIOs. The PIOs are purpose-built to provide extremely precise timing with 8 nS resolution.

The software is extremely straightforward: Set the Polarity GPIO line 104 (connected to IN), turn on the GPIO's associated with the bridge 102 enable lines (INH) line 106, wait, toggle the polarity GPIO line (IN), wait, turn off the GPIO enable (INH) lines 106. This produces one bipolar pulse. Repeat this for each pulse desired. Recommended pulse timing is 125 µS for each polarity.

This type of code would be obvious to anybody skilled in microcontroller software. Suitable code was written using ΔI in under an hour.

5) The Outer Housing:

The housing 24 will look like FIG. 3A and FIG. 3B. The exterior shape is purely aesthetic and is unimportant to the functioning of this invention. It should secure the internal applicator 10 and electronics and it should provide openings 31 for: 1) the power connector 2) the foot 11 to be inserted and removed from the applicator's 11 proximal end 14, 3) the applicator's toe opening 12 (if desired), 3) the power connector, and 4) controls or buttons 23 desired (a start/stop button and perhaps display).

The housing 24 can be designed in CAD and printed on a 3D printer. How to do this would be well understood by a CAD designer with 3D printing experience.

Alternative Embodiments

While the preferred embodiment is most preferred, alternative embodiments may provide benefits for differing objectives.

The quantity of coils 13 doesn't impact the principle of the present invention. As few as three coils 13 provide the benefits of this invention, and more coils 13 add treatment power in a nearly linear relationship. An example of a 22-coil applicator which has 60% more power is shown in FIG. 7A. It would be possible to have far more coils 13, fifty or more, for a clinical model where greater power was desired. The choice of coil 13 quantity is therefore a tradeoff between economy and performance.

The generally preferred arrangement of the coils 13 is that they be conventionally wound as discrete coils where they are positioned side-by-side, as illustrated in FIG. 1, FIG. 6B, FIG. 7A, and FIG. 7B.

Figure 12:
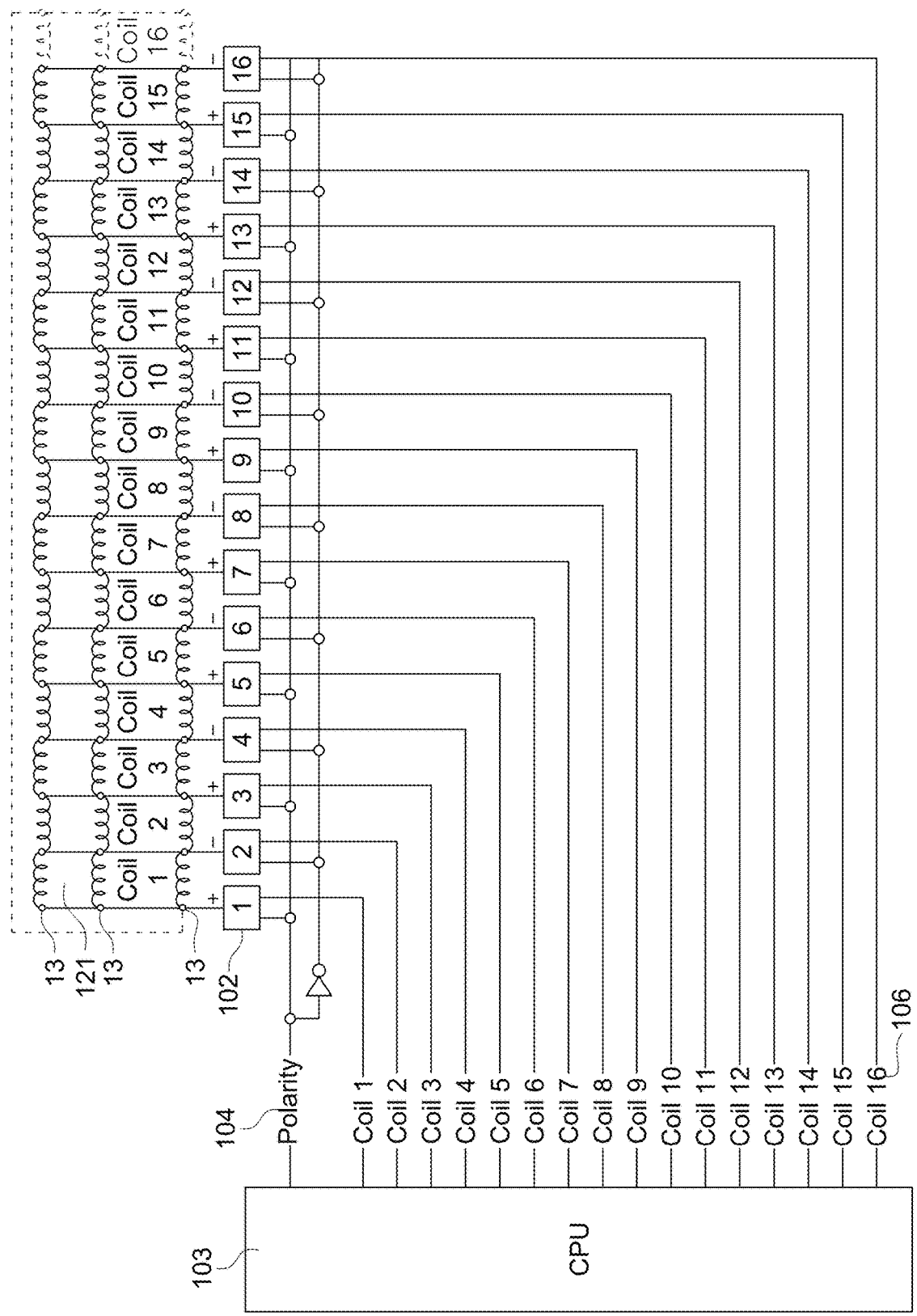
FIG. 12 is similar to FIG. 11 except that each coil 13 has multiple windings. Each coil in FIG. 12 is shown with three windings, such as a two-applicator system where one winding is for the right-side applicator, one winding for the left-side applicator, and a third winding for self-testing functionality. This illustrates that the present invention can be configured in a variety of alternative embodiments.
Figure 13:
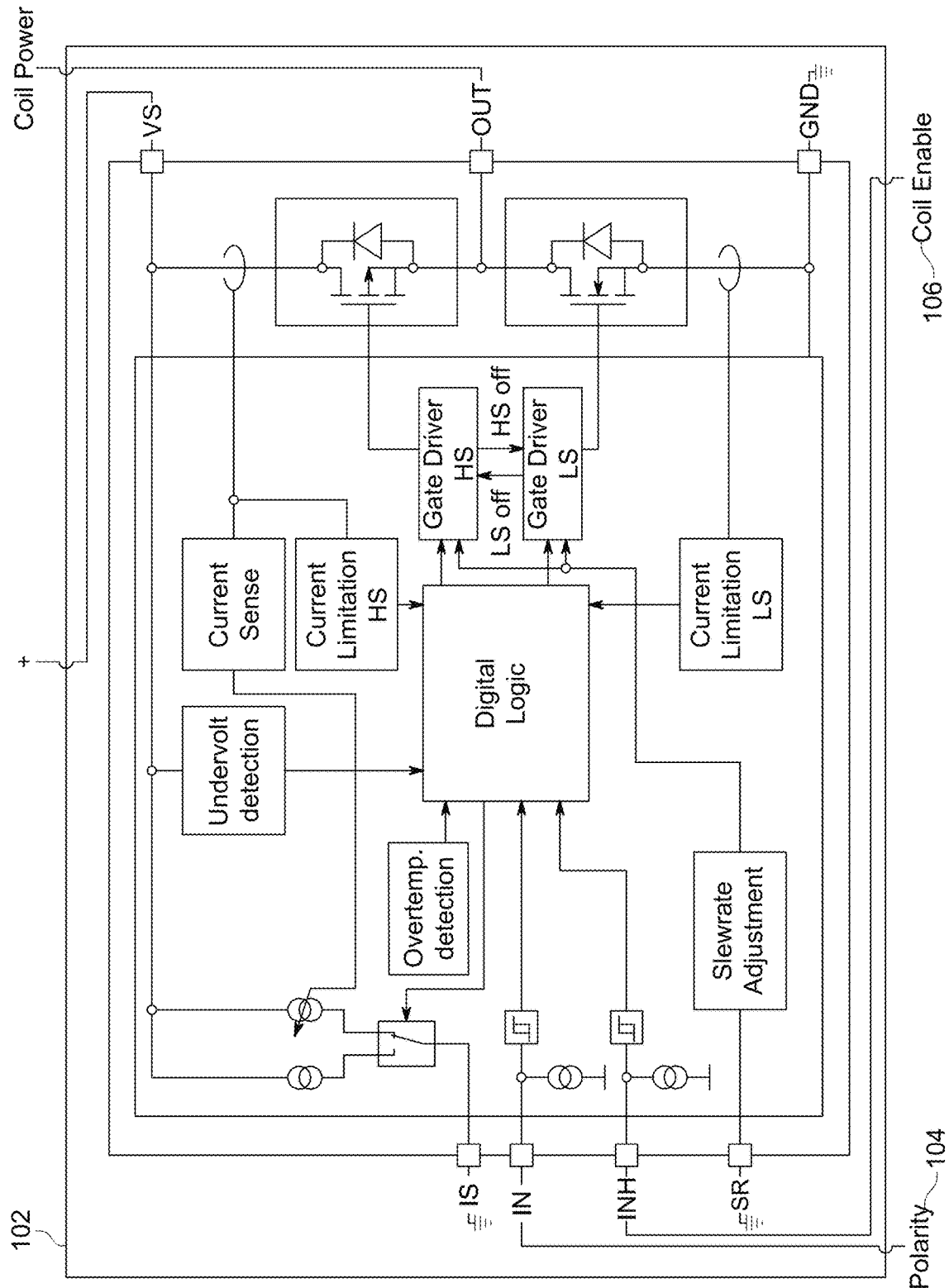
FIG. 13 shows the logical functions of the bridges 102 that were indicated by a box numbered 1 through 16 or "Common" 101 in FIGS. 10 through 12. This is illustrative of a typical bridge circuit and is intended to show typical functionality without intending to limit the design to exactly this functionality. This is illustrative of components such as the BTS7960B and indicates that two simple controls (enable 106 (INH) and polarity 104 (IN)) are all that is necessary to accomplish full bridge functionality.

Many alternative coil winding and arrangement styles are possible while still keeping the principle and benefits of the invention. A non-exhaustive list of examples would be:

1) Parallel-wound coils: Multiple individual coils are wound with their wires parallel to each other throughout the winding. Each coil remains discrete at the ends.
2) Layered coils: Multiple coils are wound one on top of the other in layers, instead of side-by-side.
3) Elongated coils/Motor-winding style: The normal circular coil is elongated, usually to the length of the solenoid, and each winding typically entails a slight rotation along the axis of the core of the solenoid, such that the coil forms something resembling a ball of string or in some ways a skein of yarn. Variations of this are often used for winding motors.
4) Loose course bobbin coil: The windings of each coil are not immediately adjacent and are somewhat spaced out and usually the windings cover a substantial portion of the length of the solenoid, most typically spiraling up and then down from end to end. While generally a sub-optimal style of winding it can be beneficial under some specific pulse applications.
5) Perpendicular coil: Typically, the treatment zone exists with the coils encircling the applicator and portion of the appendage being treated which sits within the encircled area. However, it is possible for the appendage to be inserted into the core through the side of the solenoid. In this configuration the coils in the generally center of the solenoid are either spaced wide enough for the appendage to pass between them, or the coils are bent around the appendage opening, much like a traffic circle where the appendage is in the island and straight traveling traffic veers around the island before continuing straight. This can somewhat resemble a Helmholtz coil except that a plurality of coils on either side have an additive effect, increasing the flux density. Thus, the performance still resembles a solenoid, albeit with an opening on the side.
5) Hybrid coil: a "logical coil" is wound as multiple physical windings that resemble coils (FIG. 12). Despite having multiple windings, it is considered for the purposes herein as a single "coil". A good application of this would be for one winding to be on the left applicator and a second winding to be on the right applicator with both windings wired either in parallel or series and sharing the same bridges. Such a hybrid coil would economically allow both feet to be concurrently treated without requiring twice the electronics.

While the preferred embodiment is with the coils 13 wired in a multi-tap configuration (FIG. 11), they can be connected in a shared-leg fashion (FIG. 10) if they will primarily be used selectively and not all be concurrently energized. Or, each coil 13 could have its own dedicated pair of bridges 102 (FIG. 11 with even numbered coils eliminated.) Or, coils 13 could be wired in series or parallel 121, such as in the "Hybrid coil" mentioned above and as shown in FIG. 12. Alternative coil configurations, placement, and wiring all can utilize the principles and benefits of the invention.

Figure 5A:
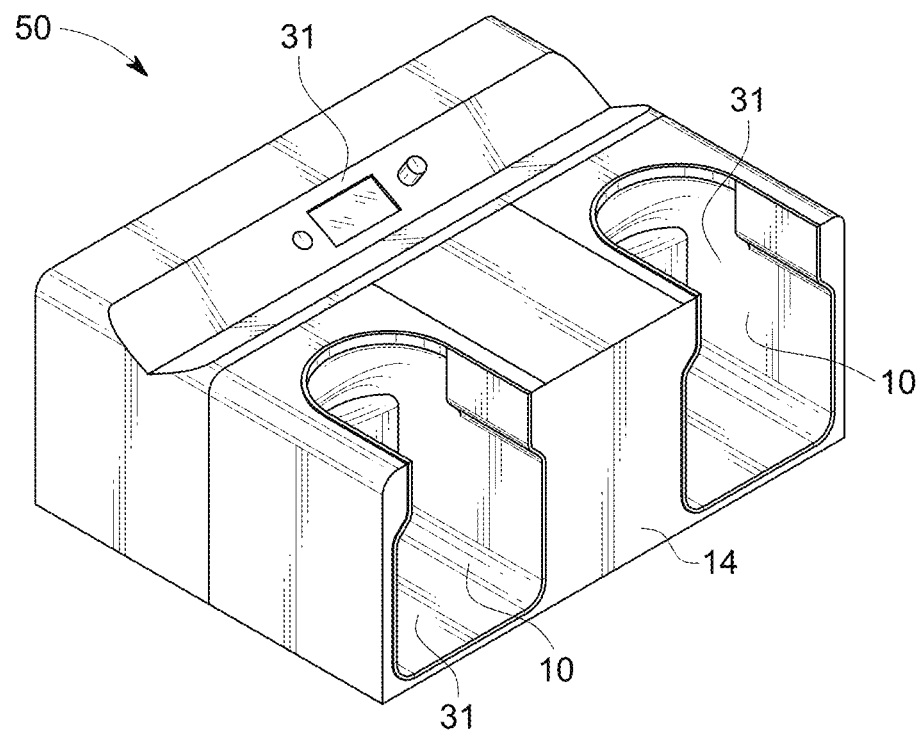
FIG. 5A is a perspective view from the proximal (heel and insertion) end 14 of the invention configured with two applicators 10, one for each foot. The openings wherein the feet may be inserted 31 through the housing and into the applicator is apparent.
Figure 5B:
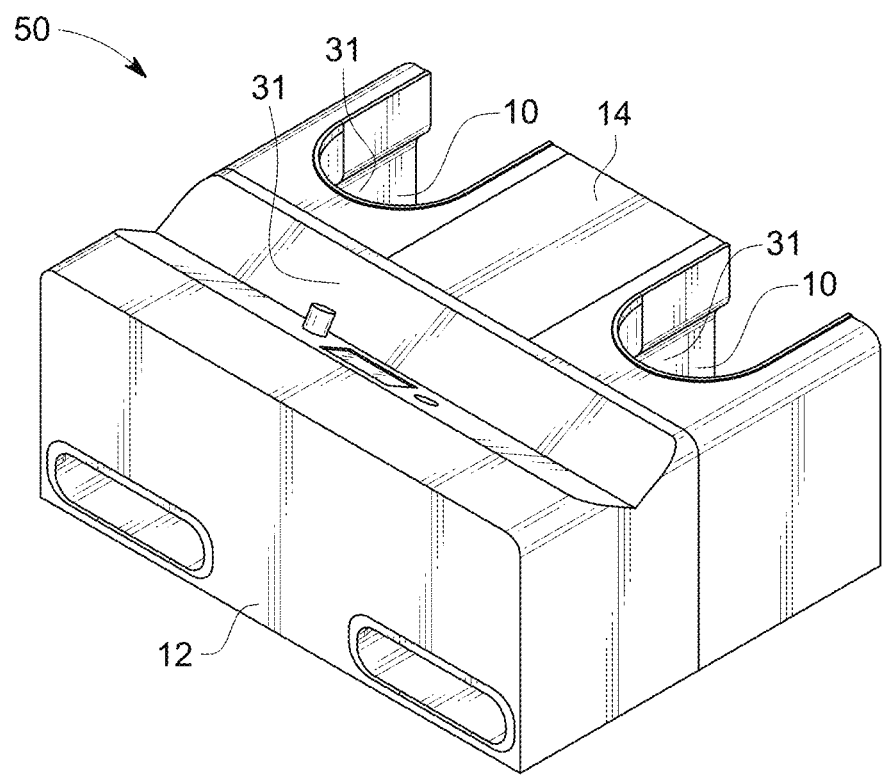
FIG. 5B is a perspective view of the same device shown in FIG. 5A from the distal (hallux/toe) end 12 of the device.

Previously, an alternative embodiment disclosed how dual applicator 50 configurations can incorporate the principles and benefits of the current invention. Two such alternative embodiments include:

1) Two single-foot applicators 20 (FIG. 2).
2) Two applicators 10 within a single housing 50 (FIG. 5A and FIG. 5B).

Figure 8:
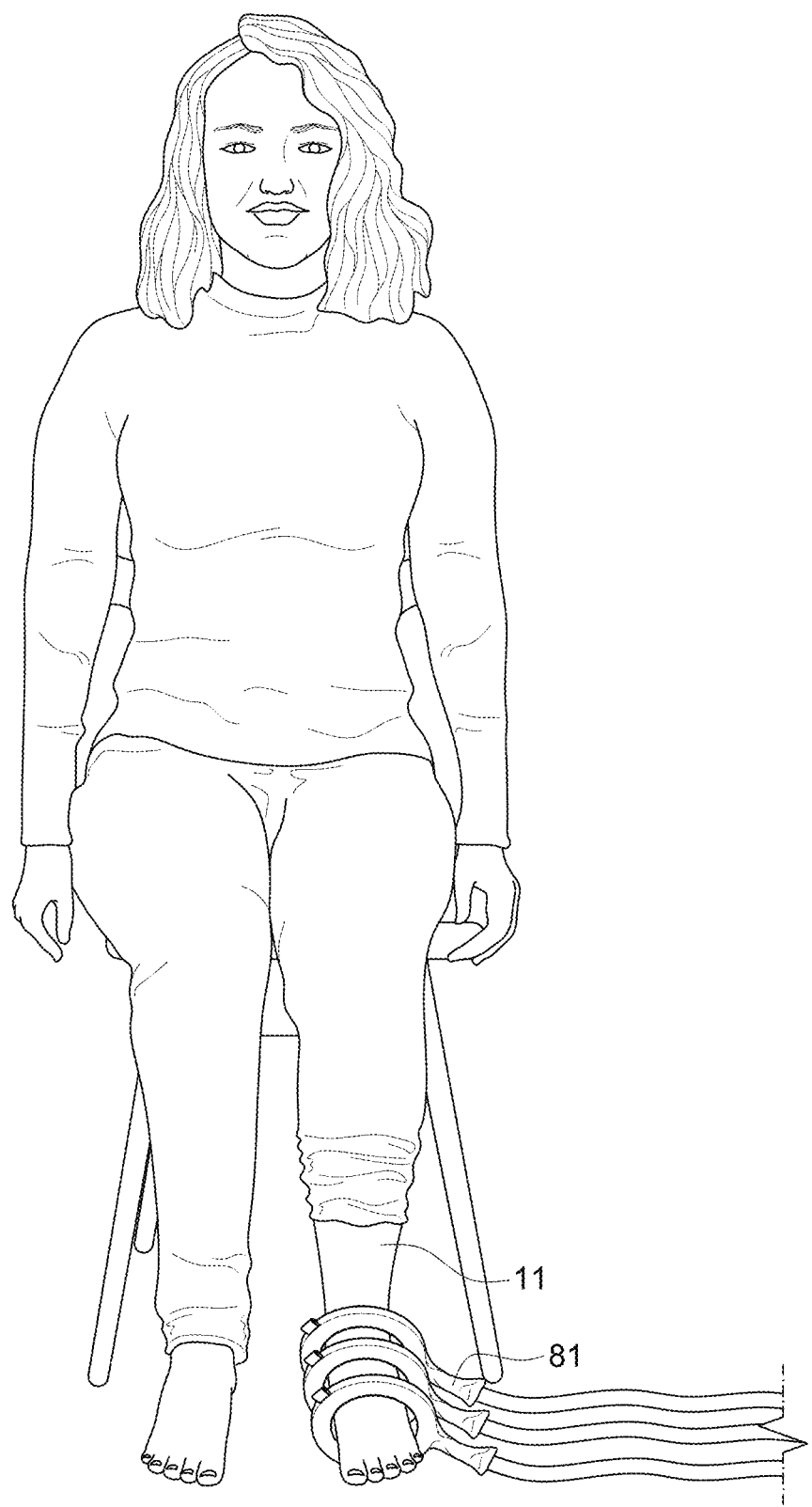
FIG. 8 shows three loop-style applicators placed onto a foot 11 with axial alignment, in close proximity, and suitable for forming an operative solenoid when energized. This arrangement is also called a "stacking ring" formation.

The applicator 10 structure itself can have alternative embodiments. One possible arrangement is shown in FIG. 8 where three (or more) loop style (individually manipulable) applicators 81 are slid onto a foot such that they have the same polarity and operatively form a solenoid. Or a multiplicity of axially-aligned coils could be sewn into a cuff that slides onto an arm or leg. These alternative embodiments lack some of the benefits that stem from the preferred embodiment that has an integrated housing featuring automatic and perfect alignment, but they may offer economy or convenience while still benefitting from the use of core flux, the additive effect of adding axially aligned coils, achieving strong magnetic flux using a safe low voltage, and a large treatment volume.

Even high-power systems can benefit from this invention by utilizing the foot applicator 10 that is easy for a foot to slide in and out of, that self-aligns the inserted foot 11, and that can spread power uniformly across a very large treatment area through the use of a multiplicity of coils 13, each with a far lower inductance than one long coil would have.

The principles and benefits of the current invention are independent of the specific choice of voltage. The preferred embodiment uses 24 volts because it presently represents the best combination of low cost and readily available components and adequate performance. Any voltage under 120 volts DC is still considered to be an ELV for medical device purposes, and it is conceivable that 36 or 48 volts may become optimal choices.

No matter what alternative embodiment is implemented, the present invention advances magnetic pulse therapy by introducing an MPTD that has a convenient and reliable applicator 10, that produces medically effective levels of highly coherent and potent flux, that can be powered using safe low voltages, and that can be self-administered in-home. Millions of people who suffer from severe chronic pain can benefit from this invention.

What is claimed is:

1. A magnetic pulse therapy device comprising:
an applicator having a cavity accessible through a proximal opening, wherein the proximal opening is configured to receive a human foot;
three or more coils in a multi-tap configuration disposed circumferentially around the applicator; and
an electronic controller operable to supply electrical pulses through the three or more coils.

2. The device of claim 1, wherein the applicator is tapered at a distal end.

3. The device of claim 1, further comprising an outer housing which encloses at least a portion of the applicator and at least a portion of the electronic controller while maintaining the opening.

4. The device of claim 1, wherein the applicator's shape positions the human foot within a core of the three or more coils.

5. The device of claim 1, wherein the proximal opening enables donning and doffing without requiring manual grasping, manipulation, or assistance.

6. The device of claim 1, further comprising:
a second magnetic pulse therapy device, communicatively coupled, physically coupled, or both, to the device of claim 1; and
wherein the combined devices form a dual-applicator system capable of concurrently treating two separate human feet.

7. The device of claim 1, wherein the three or more coils deliver a plurality of magnetic pulses to a heel, an ankle, or both simultaneously.

8. The device of claim 1, wherein the pulses supplied to the three or more coils in the multi-tap configuration are extremely low voltage, having a nominal voltage that does not exceed 50V AC or 120V DC.

9. The device of claim 1, wherein the plurality of coils comprises an alternative coil winding configuration selected from the group consisting of parallel-wound coils, layered coils, elongated coils, loose course bobbin coil, perpendicular coil, hybrid coil, stacking ring, and Helmholtz coil.

10. A magnetic pulse therapy device comprising:
an applicator having a cavity and a proximally located opening into the cavity for receiving a human foot;
a plurality of three or more coils disposed circumferentially around the applicator; an electronic controller operable to supply electrical pulses through the plurality of three or more coils; and
an outer housing which encloses at least a portion of the applicator and at least a portion of the electronic controller while maintaining the opening.

11. The device of claim 10, wherein the applicator is tapered at a distal end.

12. The device of claim 10, wherein the applicator's shape, when the human foot is fully inserted, aligns the inserted foot within a treatment zone.

13. The device of claim 10, wherein the opening enables donning and doffing without requiring manual grasping, manipulation, or assistance.

14. The device of claim 10, further comprising:
a duplicate second magnetic pulse therapy device, communicatively coupled, physically coupled, or both, to the first device of claim 10; and
wherein the combined devices form a dual-applicator system capable of concurrently treating two separate human feet.

15. The device of claim 10, wherein the three or more coils deliver a plurality of magnetic pulses to a heel, an ankle, or both simultaneously.

16. The device of claim 10, wherein the electrical pulses supplied to the plurality of three or more coils are extremely low voltage, having a nominal voltage that does not exceed 50 V AC or 120V DC.

17. The device of claim 10, wherein the plurality of three or more coils comprises an alternative coil winding configuration selected from the group consisting of parallel-wound coils, layered coils, elongated coils, loose course bobbin coil, perpendicular coil, hybrid coil, stacking ring, and Helmholtz coil.

18. A magnetic pulse therapy device comprising;
a shoe-shaped enclosure having a cavity accessible through an opening;
an operative solenoid disposed around an exterior of the shoe-shaped enclosure;
a means of connecting an electronic circuit to the operative solenoid;

wherein the enclosure is configured to receive a foot through the opening and allow the foot to slide in and out;

an outer housing which encloses at least a portion of the enclosure and at least a portion of the electronic circuit while maintaining the opening; and wherein the opening enables donning and doffing without requiring manual grasping, manipulation, or assistance.

19. The device of claim 18, further comprising an electronic circuit to power the operative solenoid.

20. The device of claim 19, wherein the operative solenoid delivers a plurality of magnetic pulses to a heel, an ankle, or both simultaneously.

21. The device of claim 20, wherein the electrical pulses supplied to the operative solenoid are extremely low voltage, having a nominal voltage that does not exceed 50V AC or 120V DC.

22. The device of claim 18, wherein the enclosure's shape, when the foot is fully inserted, aligns the inserted foot within a treatment zone.

23. The device of claim 18, further comprising:

a second magnetic pulse therapy device, communicatively coupled, physically coupled, or both, to the first device of claim 18; and wherein the combined devices form a dual-applicator system capable of concurrently treating two separate human feet.

24. The device of claim 18, wherein operative solenoid comprises an alternative coil winding configuration selected from the group consisting of parallel-wound coils, layered coils, elongated coils, loose course bobbin coil, perpendicular coil, hybrid coil, stacking ring, and Helmholtz coil.

25. A magnetic pulse therapy device comprising:

an operative solenoid comprised of three or more coils;

the operative solenoid formed such that the core of the operative solenoid can accommodate a segment of a foot;

wherein the segment of the foot may be donned and doffed within the core of the operative solenoid without requiring manual grasping, manipulation, or assistance; and a means of connecting an electronic circuit to the three or more coils forming the operative solenoid.

26. The device of claim 25, wherein the three or more coils are wired in a multi-tap configuration.

27. The device of claim 25, wherein the pulses supplied to the operative solenoid are extremely low voltage, having a nominal voltage that does not exceed 50V AC or 120V DC.

28. The device of claim 25, further comprising:

a duplicate second magnetic pulse therapy device, communicatively coupled, physically coupled, or both, to the device of claim 25; and wherein the combined devices form a dual-applicator system capable of concurrently treating two separate feet.

29. The device of claim 25, wherein the device is tapered at a distal end.

30. The device of claim 25, wherein one or more coils in addition to the three or more coils is positioned such that, when energized, magnetic pulses are delivered to the areas described by at least one of, or a combination of, the following paths:

(a) along a path starting at a plantar surface at a base of a heel (calcaneus) of the foot, following a medial border; passing anteriorly over a medial malleolus; continuing posteriorly across a dorsum to a lateral malleolus; and returning to the heel;

(b) along a path starting under the heel; over, across, or near an ankle; around an inner ankle; to an opposite side of the ankle; then down and under the foot; and back to the heel;

(c) along an area between the inner ankle and a proximal half of the plantar surface of the foot; or (d) along a proximal half of the plantar surface of the foot; and a dorsomedial aspect of an ankle joint.

* * * * *